US006593095B1

(12) United States Patent
Buckley et al.

(10) Patent No.: US 6,593,095 B1
(45) Date of Patent: Jul. 15, 2003

(54) DETECTION OF GPI ANCHORED PROTEINS

(75) Inventors: J. Thomas Buckley, Victoria (CA); Robert A. Brodsky, Ruxton, MD (US)

(73) Assignees: University of Victoria Innovation and Development Corporation, Victoria (CA); Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/616,430

(22) Filed: Jul. 14, 2000

Related U.S. Application Data

(63) Continuation of application No. PCT/US99/01086, filed on Jan. 19, 1999.
(60) Provisional application No. 60/071,941, filed on Jan. 20, 1998.

(51) Int. Cl.[7] .................... G01N 33/53; C12Q 1/00; G01W 33/543; C07K 14/195; C12N 5/00
(52) U.S. Cl. .................... 435/7.24; 435/4; 435/7.7; 435/7.9; 435/40.52; 435/69.1; 435/252.3; 435/254.11; 435/320.1; 435/325; 530/350; 536/23.1; 536/23.5; 436/117; 436/503; 436/969
(58) Field of Search .................... 435/4, 7.24, 7.7, 435/7.9, 69.1, 252.3, 254.11, 320.1, 325, 40.52; 530/350; 536/23.1, 23.5; 436/117, 503, 969; 422/73

(56) References Cited

U.S. PATENT DOCUMENTS

| | | | |
|---|---|---|---|
| 4,178,152 A | 12/1979 | Nunogaki | |
| 4,379,850 A | 4/1983 | Ricci | |
| 4,714,672 A | 12/1987 | Rokugawa et al. | |
| 5,416,026 A | 5/1995 | Davis | |
| 5,766,872 A | 6/1998 | Cybulski | |
| 5,798,218 A | * 8/1998 | Buckley | ............ 435/7.24 |

OTHER PUBLICATIONS

Nelson et al 1997; J.B.C. 272(18) 12170–12174.*
Rosse et al., 1995 (Journal of the American Society of Hematology 86(9) 3277–3286).*
Howard et al 1982 (Biochemistry; 21, 1662–1667).*
Schoot et al 1990, Blood, 76 (5) 1853–1859.*
Diep et al 1998, J.B.C. 273(4) 2355–2360.*
Holguin et al, 1989, J.Clin.Invest, 84; 1387–1394; abstract, type I/II/III cells.*
Ninomiya 1994, (Rinsho Ketsueki 35 (4) 352–357).*
Alfinito et al., "Blood Cell Flow Cytometry in Paroxysmal Nocturnal Hemoglobinuria: A Tool for Measuring the Extent of the PNH Clone," *Leukemia* 10:1326–1330 (1996).
Brodsky et al., "Resistance of Paroxysmal Nocturnal Hemoglobinuria Cells to the Glycosylphosphatidylinositol–Binding Toxin Aerolysin," *Blood* 93:1749–1759 (1999).
Hall et al., "The Use of Monoclonal Antibodies and Flow Cytometry in the Diagnosis of Paroxysmal Nocturnal Hemoglobinuria," *Blood* 87:5332–5340 (1996).
Lesleur et al., "Membrane Insertion: The Strategies of Toxins (Review)," *Molecular Membrane Biology* 14:45–64 (1997).

(List continued on next page.)

*Primary Examiner*—James Housel
*Assistant Examiner*—Padmavathi Baskar
(74) *Attorney, Agent, or Firm*—Klarquist Sparkman, LLP

(57) ABSTRACT

The present invention relates to toxins that specifically bind to GPI anchored proteins. More specifically, the present invention encompasses the uses of such toxins to detect the presence or absence of GPI anchored proteins. In one embodiment the present invention can be used to detect the presence of paroxysmal nocturnal hemoglobinuria.

15 Claims, 11 Drawing Sheets

OTHER PUBLICATIONS

Database for MEDLINE on Dialog, US National Library of Medicine (Bethesda, MD, USA), No. 94300805, Ninomiya, H. Clinical Features and Diagnosis of Paroxysmal Nocturnal Hemoglobinuria: Correlates with the Deficiency of GPI–Anchored Membrane Proteins, Rinsho Ketsueki (Japan). Abstract, Apr. 1994, vol. 35, No. 4, pp. 352–357, see Abstract.

Parker et al., "Aerolysin—The Ins and Outs of a Model Channel–Forming Toxin," *Mol. Microbiol.* *19*(2):205–212 (1996).

Tooze et al., "The Novel Monoclonal Antibody By 114 Helps Detect the Early Emergence of a Paroxysmal Nocturnal Hemoglobinuria Clone in Aplastic Anemia," *Exp. Hemotol.* *23*:1484–1491 (1995).

* cited by examiner

FIG. 4A (graph: Absorbance vs Aerolysin dilution from 1:2048 to 1:32)

FIG. 4B (graph: Absorbance vs Minutes, curves labeled 85%, 80%, 32%, 20%, 8%, 0%, Normal)

T cells Aerolysin and PI straining
T cells CONTROL

T cells Aerolysin and PI straining
T cells w/ Aerolysn 60min.

T cells w/ Aerolysin mutant straining
T cells CONTROL

T cells w/ Aerolysin mutant straining
T cells 1:1000 mutant

ABSTRACT

DETECTION OF GPI ANCHORED PROTEINS

CROSS-REFERENCE TO RELATED APPLICATIONS

This application is a continuation of PCT Application No. PCT/US99/01086, filed Jan. 19, 1999, and claims the benefit of U.S. Provisional Application No. 60/071,941, filed Jan. 20, 1998, which applications are herein incorporated by reference.

ACKNOWLEDGMENT OF GOVERNMENT SUPPORT

This invention was made with U.S. government support under CA74990 and CA70970 awarded by the PHS. The U.S. Government has certain rights in the invention.

FIELD OF THE INVENTION

The invention relates to the discovery that certain biological toxins specifically bind to the glycosylphosphatidylinositol (GPI) anchor component of certain cell-surface proteins. Applications of this discovery include the detection and diagnosis of paroxysmal nocturnal hemoglobinuria.

BACKGROUND AND SUMMARY OF THE INVENTION

Aerolysin is a channel-forming cytolytic protein produced by virulent Aeromonas species, such as *Aeromonas hydrophila*. Aerolysin is one of the best studied of all of the bacterial cytolytic toxins. It is known to be secreted as a 52 kDa precursor called proaerolysin; this precursor form is converted to the active form by proteolytic removal of a C-terminal peptide. Many eucaryotic proteases can activate proaerolysin, as can proteases secreted by *A. hydrophila* itself. Once bound to a susceptible cell, aerolysin is transformed into an insertion-competent state by oligomerization. The oligomers, which are heptameric, bridge the lipid bilayer, producing discrete 1 nm channels which result in cell lysis.

It was previously believed that aerolysin bound specifically to certain proteins found on the cell surface, such as the Thy-1 antigen (see U.S. Pat. No. 5,798,218). The present invention, however, is founded on the discovery that the target for aerolysin binding is not any particular cell surface protein, but is actually the glycosylphosphatidylinositol (GPI) anchor that is a component of many cell surface proteins. As their name suggests, GPI anchors function to anchor proteins into the cell membrane; typically the GPI anchor component is at least partly embedded in the membrane, permitting the extracellular component of the protein to be presented to the surrounding environment.

Since GPI anchors are components of many important cell surface proteins, this discovery permits the detection of such proteins (or the determination of their absence) through the use of specific binding assays. For example, since aerolysin typically lyses cells following binding to the GPI anchored protein, one such assay is based on the differential rates of lysis observed when aerolysin is mixed with cells that either have, or do not have GPI anchored surface proteins. While such assays may be performed using aerolysin, other toxins that are related to aerolysin may also be employed for such methods. Such toxins include *Clostridium septicum* alpha toxin (Parker et al., 1996), and enterlobin (a cytolytic protein produced by the Brazilian tree Enterolobium, Sousa et al., 1994). The binding specificity of these toxins and the use of this specificity to detect GPI anchored proteins is of particular clinical relevance for the disease paroxysmal nocturnal hemoglobinuria (PNH).

PNH is an acquired hematopoietic stem cell disorder manifested by abnormal hematopoiesis, complement-mediated intravascular hemolysis and a propensity toward thrombosis (Rosse, 1997). The disease usually results from a somatic mutation in the X-linked gene, PIGA (Miyata et al, 1993; Takeda et al., 1993; Miyata et al., 1994; Bessler et al., 1994) The product of the PIGA gene is necessary for the first step in the biosynthesis of GPI anchors. Hence, cells harboring PIGA mutations are characterized by a deficiency, absolute or partial, of all proteins affixed to the cell membrane by GPI anchors. The cells affected by this mutation include erythrocytes, granulocytes, monocytes and lymphocytes. PNH is closely associated with a range of hematological disorders, including aplastic anemia, certain leukemias and myelodysplasic syndrome, and assays for the disease are routinely performed for patients manifesting hematological disorders.

GPI anchored proteins have been shown to be involved in a wide range of important cell functions, including signal transduction (Robinson, 1991; Stefanova et al., 1991 ), and trafficking of apically expressed epithelial proteins (Brown et al., 1989; Powell et al., 1991). They may also play a role in regulating apoptosis (Brodsky, 1997). Two GPI anchored proteins, CD55 (decay accelerating factor) and CD59 (membrane inhibitor of reactive lysis), normally protect cells from the action of homologous complement, and it is their absence that leads to the hemolytic anemia associated with PNH (Rosse, 1982; Rosse, 1995).

The initial mutation of the PIGA gene occurs in a pluripotent hematopoietic stem cell. This cell subsequently divides and gives rise to multiple hematopoietic lineages. These various lineages generate lymphocytes, such as B cells and T cells, leukocytes and erythrocytes, all of which may be GPI anchor deficient (Rosse, 1997). Therefore, in a blood sample from a PNH patient there will be both GPI anchor deficient lymphocytes (those derived from the affected stem cell), as well as normal lymphocytes (those derived from an unaffected stem cell). Furthermore, cells derived from the affected stem cell generally fall into one of three categories. These categories are defined by the cells sensitivity to complement (I=normally sensitive cells, II=cells of intermediate sensitivity, and III=very sensitive cells).

Another characteristic of PNH is a decrease in erythrocyte survival (Rosse, 1971), and a normal or even increased survival of granulocytes (Brodsky, 1997: Horikawa et al., 1997; Brubaker et al., 1977). This decrease in erythrocyte survival poses a problem to clinicians because the two most popular methods of diagnosing PNH, the Ham's test and the sucrose hemolysis test, involve isolating erythrocytes and measuring their sensitivity to homologous complement. Because of decreased erythrocyte survival in PNH patients, the results from these assays do not provide accurate information about the percentage of affected blood cells. Furthermore, these assays are relatively insensitive and may not detect small populations of PNH cells, such as may be present at the early stages of the disease.

In addition to the Ham's test and the sucrose hemolysis test, flow cytometry is sometimes used to diagnose PNH. Flow cytometry offers the clinician the ability to use monoclonal antibodies to a variety of different GPI anchored proteins. These antibodies can be used to detect GPI anchored proteins on a variety of different cell types. For example, monoclonal antibodies to CD59 can be used to detect GPI anchors on granulocytes and other cells, thus providing a more accurate assessment of the number of PNH affected cells. Unfortunately, however, flow cytometry requires expensive equipment and significant technical expertise that is not available in many laboratories. Additionally, while flow cytometry can be significantly more sensitive than the sucrose hemolysis and Ham's tests, it cannot be routinely used to detect PNH cells in populations of less than 1–2% of total cells (Schubert et al., 1991; Hall et al., 1996). Therefore, there is a need for an assay that is inexpensive, accurate and specific for the detection of small populations of PNH affected cells, and the present invention provides such an assay.

The invention provides a number of ways of detecting the presence of PNH cells in biological samples. Generally, these methods comprise contacting a biological sample containing blood cells with a toxin that specifically binds to GPI anchored proteins, and monitoring binding of the toxin to the blood cells. In view of the specificity of the toxin, decreased binding of the toxin to the blood cells compared to binding observed with a control blood sample indicates decreased GPI anchored proteins, and thus the presence of PNH cells.

The biological sample will typically be taken from an individual who is to be screened for PNH, and may be, for example, whole blood, granulocytes or erythrocytes. The toxin may be aerolysin, proaerolysin, Clostridium alpha toxin, enterolobin, or any other toxin that specifically binds to GPI anchored proteins. While the toxin will generally be in its naturally occurring form, forms of the toxin having an altered amino acid sequence may also be employed. For example, forms of aerolysin that bind to GPI anchored proteins, but which do not lyse cells to which they bind are known, and may be used in the assay.

Where a normal (cytolytic) form of the toxin is employed, monitoring the binding of the toxin to the blood cells may be achieved by monitoring the amount or rate of lysis of the blood cells. Typically, the blood cells in a sample taken from a healthy patient will lyse in the presence of aerolysin, since the toxin will bind to GPI anchored proteins present on the surface of such cells, and subsequently insert into the membrane, forming holes that result in cells lysis. PNH cells, on the other hand, will be resistant to lysis because of the deficit of GPI anchored proteins compared to the cells from a healthy patient. Toxin-induced lysis results in a clearing of the test fluid (decrease in optical density), and may be readily monitored by standard means, including visual inspection, microtiter plate readers or spectrophotometers.

By way of example, one embodiment of the present invention comprises an assay for PNH cells in which a range of dilutions of a suitable toxin (such as aerolysin) is utilized. Such a dilution range may be conveniently established in a microtiter plate. The blood sample to be tested is then added to the various dilutions and the mixtures are incubated. Typically, a parallel control experiment is performed in which a blood sample from a healthy individual is utilized. Following incubation, the sample and controls are compared for lysis, and the lowest concentration of toxin at which lysis is observed is noted. If the sample is observed to lyse at higher concentrations of toxin than the control (or to be resistant to lysis), then the patient from whom the sample was taken may be considered to be at risk of having PNH, and further investigation is warranted.

Representative ranges of toxin concentrations that can be used in such an assay are for example, 1 M toxin to $1\times10^{-11}$ M toxin, $1\times10^{-4}$ M toxin to $1\times10^{-11}$ M toxin, and $1\times10^{-6}$ M toxin to $1\times10^{-10}$ M toxin. The number of different dilutions used can vary depending on the degree of precision desired. In other words very small increments between two sequential dilutions can be used to provide more precise results. Conversely, a rough estimate of toxin resistance can be determined using as few as two different concentrations of toxin.

In another embodiment of the invention, a sample can be treated with a toxin specific for GPI anchored proteins and the rate of lysis can be determined by measuring optical density at various time points. A sample of cells having a high concentration of GPI anchored proteins will lyse more quickly than a sample of cells having a low concentration of GPI anchored proteins. Therefore, comparing the rate of lysis observed with the rate observed with a control permits the relative concentration of GPI anchors to be determined.

Alternatively, the binding of a toxin specific to GPI anchored proteins may be detected and/or quantified by employing a form of the toxin conjugated to a detectable label (such as a fluorescent or radioactive label). Detection of the cell-toxin-label complex may then be accomplished by any standard means, including flow cytometry and fluorescence activated cell sorting (FACS). Such assays are typically best performed where lysis of the cells is avoided; this may be achieved by using a non-cytolytic form of the toxin (such as the precursor form, or a mutant), or by performing the assay at a reduced temperature (e.g., 4° C. or less) at which the toxin will bind to GPI anchored proteins, but will not cause cell lysis.

In a further embodiment of the invention, a cytolytic toxin that specifically binds to GPI anchored proteins, such as aerolysin, can be used to enhance the sensitivity of other PNH assays, such as flow cytometry as described by Hall and Rosse (1996). Since aerolysin will preferentially lyse normal (i.e., non PNH) cells in the sample, pre-incubation of the sample with aerolysin will increase the relative concentration of PNH cells, making such cells more easily detected by the assay.

In addition to methods for detecting PNH cells, the present invention provides methods for generally detecting or quantifying the presence of GPI anchored proteins in a biological sample. Such methods typically comprise contacting the biological sample with a toxin that specifically binds to GPI anchor-containing proteins and detecting or quantifying the binding of the toxin to GPI anchored proteins. Detecting or quantifying the binding of the toxin to GPI anchored proteins may be accomplished by methods including detecting lysis of cells (if a cytolytic form of toxin is employed), or detecting the presence of a detectable label in a GPI anchor/toxin/label complex.

The methods provided by the invention may further be used to distinguish between cells having GPI anchored proteins (GPI$^+$ cells) and cells lacking GPI anchored proteins (GPI$^-$ cells), and may be applied to separate and sort such cells. By way of example, a cell mixture may be incubated with a non-cytolytic form of aerolysin conjugated to a fluorescent marker. Following binding of the aerolysin to GPI anchored proteins, the cells may be separated into collections of GPI$^+$ and GPI$^-$ cells using conventional flow cytometry methods.

In another embodiment of the invention, a cytolytic toxin that specifically binds to GPI anchored proteins, such as aerolysin, can be used to detect small populations of cells that are GPI anchor deficient. Finding cells that are GPI anchor deficient can be indicative of a genetic mutation that affects the presentation of GPI anchors on the cell surface. Hence, this particular embodiment is useful for determining genetic variations that affect the expression of GPI anchored proteins prior to an actual physical manifestation of disease. Used in this way, the invention involves pre-incubating a mixture of cells with a toxin specific for GPI anchored proteins. This pre-incubation, results in lysis of the cells that express GPI anchored proteins, and effectively increases the proportion of GPI anchor deficient cells to a level that can be detected using various other means.

These and other aspects of the invention are illustrated by the following examples and descriptions.

BRIEF DESCRIPTION OF DRAWINGS

FIGS. 4A–D: show aerolysin assays for detection of PNH. (A) Dose response curve showing aerolysin sensitivity of two normal (solid lines, open symbols) versus two PNH (dashed lines, closed symbols) erythrocytes. Serial dilutions of activated aerolysin (1.5×10$^{-6}$ stock) were performed in a 96 well plate and mixed with an equal volume of 0.8% erythrocytes. Absorbance at 620 nm was measured after 10 minutes at 37° C. using a plate reader. (B) Kinetic analysis of aerolysin-induced hemolysis of normal erythrocytes (bottom line) and erythrocytes from 5 different PNH patients. The rate of hemolysis was determined by measuring the change in optical density of erythrocytes at 600 nm and 37° C. as a measure of time using a spectrophotometer. (C) Flow cytometric analysis for CD59 expression of PNH red blood cells from the patient with 8% type III PNH erythrocytes (solid line) and a normal control (dotted line). (D) Flow cytometric analysis for CD59 expression of PNH red blood cells from the patient with 80% PNH erythrocytes (solid line) and a normal control (dotted line). The majority of cells represent type II PNH erythrocytes.

FIGS. 6A and C show flow cytometric analyses for CD59 expression of LD$^-$ and JY5 cells before (solid line) and after (dotted line) stable transfection of the PIGA cDNA. FIG. 6B is a graph showing viability of LD$^-$ (solid line) and LD$^-$PIGA$^+$ (dotted line) cells following exposure to 1 nM aerolysin at 37° C. FIG. 6D is a graph showing viability of JY5 (solid line) and JY5PIGA$^+$ (dotted line) cells following exposure to 1 nM aerolysin at 37° C. Cell viability was determined in triplicate at five minute intervals by trypan blue exclusion. Error bars represent standard deviations.

FIG. 8A shows flow cytometric analyses for CD59 expression in cell populations consisting of 90% LD$^-$PIGA$^+$ cells and 10% LD$^-$ cells (solid line) and 100% LD$^-$ cells (dotted line).

FIG. 11A shows flow cytometry results for control cells (not treated with aerolysin) stained with propidium iodide. FIG. 11B shows cells exposed to aerolysin a 1:1000 dilution of 1.5×10$^{-9}$ M aerolysin for 60 minutes at 37° C. and stained with propidium iodide. FIG. 11C shows control cells without treatment with aerolysin and without staining. FIG. 11D shows flow cytometry results after treatment for 60 minutes at 37° C. with the aerolysin mutant Thy 253 Cys/Ala 300 Cys conjugated to Alexa 488 (Molecular Probes, Eugene, Oreg.).

FIGS. 12A and C show control bone marrow cells including red blood cells, without conjugated toxin (12A), and with conjugated toxin (12C). FIGS. 12B and D show control bone marrow cells with the red cells gated out, without conjugated toxin (12B), and with conjugated toxin (12D).

SEQUENCE LISTING

Figure 1:
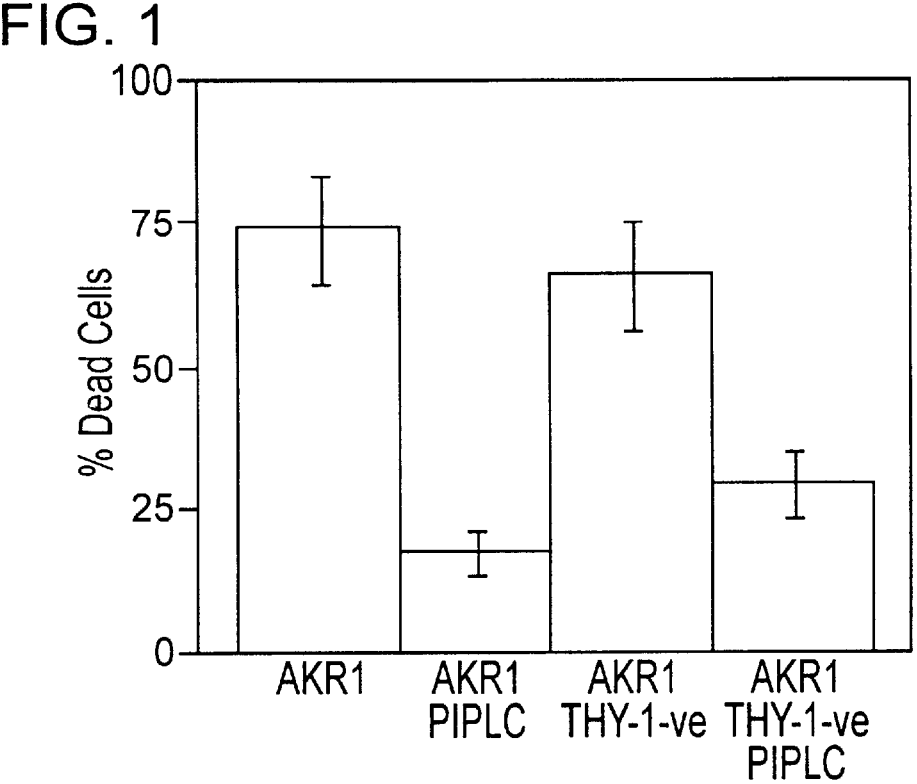
FIG. 1 shows that mouse lymphocytes contain more than one GPI anchored aerolysin receptor. Sensitivity of AKR1 (Thy-1-) cells to aerolysin is compared to sensitivity of Thy-1$^+$ cells before and after treatment with PI-PLC as described in the methods. Bars represent the SEM of five separate experiments.

Seq. ID No. 1: shows the nucleotide sequence of the aerolysin gene from *Aeromonas hydrophila* and the amino acid sequence of the encoded protein.

Seq. ID No. 2 and Seq. ID No. 3: show PCR primers useful for amplifying the open reading frame of the aerolysin gene.

Seq. ID No. 4 and Seq. ID No. 5: show PCR primers useful for amplifying the DNA sequence encoding the mature Thy-1 peptide from mouse.

Seq. ID No. 6 and Seq ID No. 7: show PCR primers useful for amplifying the cDNA encoding the human Thy-1.

DETAILED DESCRIPTION

Definitions

Glycosylphosphatidylinositol (GPI) anchored proteins: are found on the external surfaces of eucaryotic cells (McConville and Ferguson 1993; Englund 1993; Hirose et al., 1995). GPI anchors typically contain a core of ethanolamine-HPO4-6Man$\alpha$1-2Man$\alpha$1-6Man$\alpha$1-4GlcN$\alpha$1-6myo-inositol-1HPO4-diacyl-glycerol (or alkyla-cylglycerol or ceramide; McConville et al., 1993). However, a number of variations on this core structure have been reported. For example, other sugars may be added to the glycan core, and in human erythrocyte GPI anchored proteins such as acetylcholinesterase, the inositol may be substituted with an additional fatty acid.

Thy-1: is a GPI anchored protein found on T-lymphocytes (Seki et al., 1985).

Aerolysin: refers to a bacterial toxin produced by members of the Aeromonas family. As described herein, aerolysin binds specifically to GPI anchored proteins. As used herein, the term "aerolysin" refers not only the native toxin produced by Aeromonas species, but also to forms of this toxin produced by expressing the cloned Aeromonas aerolysin gene in other cell types, as well as mutant forms of the toxin which retain the ability to bind specifically to the GPI anchor. As shown below, both the precursor form of the toxin (referred to in the literature as "proaerolysin") and the activated form (referred to in the literature as "aerolysin") bind specifically to GPI anchored proteins and are thus encompassed within this definition of "aerolysin." The amino acid sequences of aerolysin produced by various members of the Aeromonas family are highly conserved. The nucleotide sequence of the aerolysin gene of *Aeromonas hydrophila* and the amino acid sequence of the encoded peptide as reported by Howard et al. (1987) are shown in Seq. ID No. 1. Nucleotide sequences of aerolysin genes from other members of the Aeromonas family and the corresponding amino acid sequences of the encoded proteins are known in the art and described in for example, Hirono et al., 1992; Hirono and Aoki, 1993; Husslein 1998; and Chopra et al., 1993. In addition, various mutant forms of aerolysin can readily be produced using standard mutagenesis techniques. Known mutant forms of aerolysin include non-cytolytic forms, as those described in U.S. Pat. No. 5,798,218. Thus, "aerolysin" as used herein includes all forms of the toxin which retain the ability to specifically bind to GPI anchored proteins, including mutant forms, which retain the ability to specifically bind to GPI anchored proteins.

Preferably, the aerolysin used in the present invention is in purified form. In this context, "purified aerolysin" refers to a preparation of aerolysin in which the aerolysin has been separated from substantially all of the cellular proteins (if produced by lysis of cells) or from substantially all proteins in the growth medium (if purified from growth medium following secretion by cells). Preferably, the aerolysin will represent no less than 70% of the protein content of the preparation. However, it will be appreciated that the aerolysin preparation may be constituted using a carrier protein, such as serum albumin, in which case aerolysin may represent less than 70% of the protein content of the preparation.

Mutant forms of aerolysin may be prepared which retain the characteristic of being able to bind specifically to GPI anchored proteins. Such mutant forms may be produced by site-directed or other standard mutagenesis techniques, as described in Sambrook et al. (1989).

Because the nucleotide sequences of several aerolysin genes are known (see, for example, Seq. ID No. 1), one skilled in the art will readily be able to produce the gene using the polymerase chain reaction (PCR) procedure, as described by Innis et al. (1990). Methods and conditions for PCR amplification of DNA are described in Innis et al. (1990) and Sambrook et al. (1989).

The selection of PCR primers for amplification of the aerolysin gene will be made according to the portions of the gene which are desired to be amplified. Primers may be chosen to amplify small fragments of the gene or the entire gene molecule. Variations in amplification conditions may be required to accommodate primers of differing lengths; such considerations are well known in the art and are discussed in reference Innis et al. (1990). By way of example only, the entire aerolysin open reading frame may be amplified using the following primers. Primer 1: 5' ATG-CAAAAAATAAAACTAACTGGCTTG 3' Seq. ID No. 2 Primer 2: 5' CGCTGAGGCTGACTTGAACGGAAGCCC 3' Seq. ID No. 3

Template DNA for PCR amplification to produce the aerolysin gene can be extracted from Aeromonas sp. cells using standard techniques (see Sambrook et al., 1989).

The cloned aerolysin gene can readily be ligated into bacterial expression vectors for production of the encoded aerolysin. Standard methods and plasmid vectors for producing procaryotic proteins in *E. coli* are described in Sambrook et al. (1989). These methods facilitate large scale production of the protein and, if necessary, expression levels can be elevated by placing a strong, regulated promoter and an efficient ribosome binding site upstream of the cloned gene. Protease-deficient host cells are preferred since they yield higher levels of aerolysin.

The aerolysin gene may also be cloned into a suitable vector for mutagenesis. Mutations in the aerolysin gene may result in deletions or additions to the encoded amino acid sequence, or may be substitutions of one amino acid for another.

Mutant aerolysins must still, for the purposes of this invention, be able to bind specifically to GPI anchored proteins but they might not be cytolytic (i.e., the mutation may result in the loss of the protein's ability to oligomerize or form membrane channels). As used herein, the phrase cytolytic toxin refers to a toxin that has the ability to bind to GPI anchors and the ability to cause cell lysis.

Mutant forms of aerolysin that retain binding specificity, but are non-cytolytic include: His 132 Asn (i.e., the histidine residue at position 132 mutated to asparagine); Gly 202 Cys; the double substitution Thr 253 Cys/Ala 300 Cys; and Thr 225 Gly. Mutant forms of aerolysin which are capable of specifically binding to GPI anchored proteins but which are non-cytolytic may be used to label GPI anchored proteins on cells without affecting cell viability. Such mutant are useful in cell sorting experiments, separation of cells expressing GPI anchored proteins from a mixture, and fluorescence microscopy.

While many mutant forms of aerolysin that retain the essential characteristic of GPI anchor specific binding will contain single or multiple amino acid substitutions, it will be appreciated that substantially shorter forms of aerolysin may also be produced which retain this charateristic. Such shorter forms would comprise, at a minimum, that portion of aerolysin capable of specifically binding to GPI anchored proteins.

Toxins specific for GPI anchored proteins: have the ability to specifically bind to proteins that include GPI anchors. GPI anchor specific binding means that when the toxin is combined with an antigen mixture including proteins having GPI anchors, the toxin molecules will bind substantially only to those proteins, and will generally not bind to proteins lacking GPI anchors. The determination that a toxin binds specifically to GPI anchored proteins may be made using conventional techniques. For example, a western blot may be established using the extracts from $LD^-$ cell (lacking GPI-anchored proteins) and $LD^-PIG^+$ cells (expressing GPI anchored proteins)(these cells are described further below). Incubation of the blots with the toxin is followed by detection of toxin binding with an anti-toxin antibody. A toxin that binds specifically to GPI anchored proteins will be observed to bind only to proteins from the $LD^-PIGA^+$ cells.

II General Methods

1. Biochemical Methods

Biochemical procedures described herein may be performed using standard laboratory methods as described in Molecular Cloning: A Laboratory Manual, 2nd ed., vol. 1–3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-lnterscience, New York, 1992 (with periodic updates) (hereinafter, "Ausubel et al., 1992") and Harlow and Lane, Antibodies: A Laboratory Manual, Cold Spring Harbor Laboratory, Cold Spring Harbor, N.Y., 1988 (hereinafter "Harlow and Lane, 1988"), unless otherwise noted.

2. Preparation of Aerolysin and Proaerolysin

Proaerolysin and aerolysin can be prepared in quantities sufficient for the applications described below by the method described by Buckley and Howard (1988). For example, proaerolysin can be isolated from culture supernatants of *Aeromonas salmonicida* CB3 transformed with the aerolysin gene (aerA) of *Aeromonas hydrophila* as follows. First, the culture supernatants are concentrated fifty-fold by ultra filtration and then centrifuged for two hours at 100,000×g to remove particulate matter. (*A. salmonicida* CB3 is a protease-deficient strain which can produce higher yields of aerolysin. Although protease-deficient strains are preferred since they give a higher yield of aerolysin, other transformed strains of Aeromonas, as well as other host cells and non-transformed Aeromonas strains may also be used.) The supernatant is then exchanged into 20 mM phosphate buffer containing 0.3 M NaCl, pH 6.0, by passing it down a Sephadex G25 column. The resulting mixture is then applied to a hydroxyapatite column equilibrated in the same buffer. Proaerolysin is eluted from the column with a linear gradient formed by the starting buffer and 0.2 M phosphate containing 0.3 M NaCl, pH 6.0. Peak fractions are combined and the protein is precipitated by adding ammonium sulfate to 60% of saturation at 0° C. Following centrifugation, the precipitate is dissolved in 20 mM HEPES, pH 7.4, and applied to a Pharmacia DEAE Sepharose C16B column. Finally purified proaerolysin is eluted with a linear gradient formed by the starting buffer and 20 mM HEPES, 0.4 M NaCl.

If desired, aerolysin can be produced from the purified proaerolysin either by adding trypsin to 1 μg/ml and incubating at room temperature for 10 min, or by adding 0.5 units/ml of immobilized trypsin and incubating with end over end mixing for 15 min. at room temperature. Immobilized trypsin can be removed by brief centrifugation; soluble trypsin can be inhibited by adding soybean trypsin inhibitor to 10 μg/ml.

III Aerolysin Binds Specifically to GPI Anchored Proteins

1. Methods

A. Bacterial Strains, Mammalian Cell Lines and Their Growth Conditions

*Escherichia coli* strains JM109 and BL21 (DE3)/pLysS (Novagen) were used as hosts for plasmid amplification and gene expression respectively. Both strains were grown in LB medium at 37° C. and 300 rpm using a rotary shaker. Where appropriate, ampicillin, chloramphenicol and kanamycin were added at concentrations of 100 μg/ml, 34 μg/ml and 40 μg/ml, respectively. The Chinese hamster ovary cell line (CHO-K1) and the monkey kidney cell line (COS) were purchased from the American Type Culture Collection. Murine lymphocyte cell lines AKR1 (Thy-$1^+$) and AKR1 (Thy-$1^-$ d; a class d mutant; Evans et al., 1987), as well as EL4 (Thy-$1^+$) and EL4 (Thy-$1^-$ f; a class f mutant) were generously provided by Dr. R. Hyman (Salk Institute). CHO-K1 cells were grown in F-12 nutrient mixture medium (Gibco BRL), whereas AKR1, EL4 and COS cells were grown in Dulbecco's modified Eagle's high glucose medium. Both media were supplemented with bovine fetal clone I serum (10%, v/v), streptomycin (100 μg/ml), and penicillin (100 U/ml). All cell lines were grown in 5% $CO_2$ at 37° C.

B. Plasmid Construction and Gene Expression

The PCR primers GGGAATTCCATATGCAGAAGGTGACCAGCC (Seq. ID No. 4) and CCGGAATTCAACACTTGACCAGTTTGTCTC (Seq. ID No. 5) were used to isolate the DNA sequence encoding the mature peptide of Thy-1 from the mouse cDNA clone pTZ18U.TM8.5 (Hedrick et al., 1984; also a gift from Dr. R. Hyman). The primers were designed so that the cloned gene began with an added methionine codon (ATG) to initiate translation and ended with an added stop codon (TGA). The PCR product was ligated into the prokaryotic expression vector pET29a (Novagen), to obtain plasmid pM42 which was amplified in JM109, isolated and retransformed into BL21 (DE3)/pLysS. Expression of the cloned gene was performed according to the protocol provided by Novagen. Three hours after induction with 1 mM IPTG (isopropylthio-β-D-galactoside), cells were collected by centrifugation and aliquots of resuspended cell pellets were used for the sandwich Western blotting procedure described below. BL21 (DE3)/pLysS containing pET29*a* served as a control. For expression of human Thy-1 in tissue cell lines, the cDNA encoding human Thy-1 (pThy-1H, a gift from Dr. R. Kay, University of British Columbia) was amplified by PCR using primers AAGCTTGCTGCAGCAGCGGAAGAC (Seq. ID No. 6) and CTAGAGGATCCCACCAGTCACAGGGAC (Seq. ID No. 7), and then subcloned into the eucaryotic expression vector pRcCMV (Invitrogen) to obtain pRc-Thy-1. The plasmid construct of the chimeric GPI anchored form of human cathepsin D (CD; a gift from Dr. E. Ogier-Denis, Facult, de M,decine de Xavier Bichat, Paris) has been reported earlier (Ogier-Denis et al., 1995). It contains the human CD cDNA (Horst and Hasilik, 1991) fused with the GPI anchor signal sequence of human 5'-nucleotidase (Misum et al., 1990). Plasmids were transfected into CHO-K1 cells for stable expression using a $CaCl_2$-precipitation method (Kingston, 1988), or into COS cells for transient expression using a DEAE-dextran and chloroquine method (Cullen et al., 1984). To select CHO-K1 transfectants, 500 μg/ml geneticin (G418; Gibco) was added to the growth medium. Transfected cells were collected 3 days after transfection and washed once with 4.3 mM $Na_2HPO_4$, 1.4 mM $KH_2PO_4$, pH 7.3, containing 137 mM NaCl and 2.7 mM KCl. Aliquots of resuspended cell pellets were then used to detect proaerolysin-binding proteins by sandwich Western blotting as described below. The entire insert sequence in pRc-Thy-1 and pM42 was confirmed by DNA sequencing using the chain termination method and the Sequenase kit from United States Biochem. Corp.

C. Detection of Proteins by Western Blotting

Sandwich Western blotting was used to detect proaerolysin-binding proteins as previously described in Nelson et al. (1997). Briefly, cell or protein samples were separated by SDS-PAGE and blotted onto nitrocellulose. The blots were probed with proaerolysin, followed by polyclonal anti-aerolysin antibody and anti-rabbit horseradish peroxidase. The surface protein gp63 expressed in CHO cells and in Leishmania major samples was detected with a monoclonal anti-gp63 antibody and anti-mouse horseradish peroxidase. The gp63 samples and the antibody were generously provided by Dr. R. McMaster (University of British Columbia). Their preparation has been described previously (Morrison et al., 1997). Blots were developed by enhanced chemiluminescence (Amersham Corp.).

D. Phosphatidylinositol-specific-phospholipase C (PI-PLC) Treatment and Aerolysin Sensitivity Assay For the aerolysin sensitivity assay, 1 ml of $5 \times 10^5$ cells/ml was treated with 200 mU PI-PLC (Boehringer Mannheim) for 2 h at 37° C. rotating end over end. Cells were then pelleted by brief centrifugation, the supernatant was removed and cells were resuspended in 1 ml of growth medium. Aerolysin was added to a final concentration of 0.5 nM and corresponding control samples were incubated without aerolysin for 1 h at 37° C. in 5% $CO_2$. Following incubation, samples were diluted 1:2 in 0.1% trypan blue in phosphate buffered saline (PBS; 10 mM $NaH_2PO_4$, 150 mM NaCl, pH 7.4) containing 0.1 mM phenylmethylsulfonylfluoride and 1 mM EDTA (ethylenediamine tetraacetic acid) and live/dead cell counts were performed using a hemocytometer. COS transfectants expressing the GPI-form of CD were harvested and washed once with PBS. The washed cells were treated with 350 mU PI-PLC in 150 μl of the same buffer for 2 hours at 37° C., with end-over-end rotation. Control samples were incubated without enzyme. Cells were pelleted at 90000 rpm for 30 min at 4° C. in a Beckman Airfuge. Aliquots of cells and supernatants were used for the Western blotting procedure.

E. N-glycosidase Treatment

Mouse brain homogenate, prepared as described previously (Nelson et al., 1997) was treated with PI-PLC and centrifuged. A 10 μl sample of the supernatant was mixed with an equal volume of N-glycosidase incubation buffer (40 mM $NaH_2PO_4$, 100 mM EDTA, 1% sodium dodecyl sulfate, 10% β-mercaptoethanol, pH 7.5) and the mixture was boiled for 2 min. After the mixture was cooled to room temperature, 3.3 μl of a protease inhibitor mixture (0.6 mM phenyl-methanesulfonyl fluoride, 60 μg/ml aprotinin, 120 μM leupeptin and 12 μM pepstatin A) was added, followed by 2.5 μl of 10% octylglucopyranoside and 7.5 μl of peptide-N-glycosidase F (PNGase F; Oxford Glycosystems), containing 1.5 units of the enzyme. A control incubation was also carried out in which 7.5 μl of buffer was added in place of the enzyme. After 18 hours at 37° C., sample buffer was added and aliquots were separated by SDS-PAGE and sandwich Western blotted.

F. Pronase Treatment of Thy-1 Incorporated into Liposomes

Thy-1 was purified from deoxycholate extracts of pig brain using a modification of the procedure of Letarte-Muirhead et al. (Letarte-Muirhead et al., 1975) and incorporated into carboxyfluorescein (CF)-entrapped liposomes as reported earlier (Nelson et al., 1997). Pronase was added to 500 μl of the liposomes (0.35 μmoles of lipid) to a final concentration of 500 μg/ml and the mixture was incubated for 1 h at room temperature. Liposomes incubated under the same conditions without pronase were used as a control. The liposomes were separated from free CF as well as from the fragmented protein and the pronase by passing them over a Sephacryl S-300 column. Aerolysin-induced channel formation was monitored by measuring CF release spectrofluorimetrically, as described before (Nelson et al., 1997).

G. hGPI Anchor Removal by Aqueous Hydrofluoric Acid (HF) Treatment

The GPI anchor of purified VSG was chemically cleaved from the protein by treatment with aqueous HF, following the procedure of Ferguson et al. 1988. The VSG was a kind gift from Dr. Terry Pearson (University of Victoria). The glycoprotein (150 μg) was incubated with 100 μl of 50% aqueous HF at 0° C. for 48 h. A control sample was incubated with water under the same conditions. The HF was neutralized by adding the sample to frozen saturated lithium hydroxide and the precipitate of lithium fluoride was removed by centrifugation. The pellet was washed twice with 50 μL of distilled water and the aqueous portions were combined and desalted over a PD-10 (G-25) column equilibrated in 20 mM HEPES (N-[2-hydroxyethyl]piperazine-N'-[2-ethanesulfonic acid]), pH 7.4, containing 150 mM NaCl. Proaerolysin binding was assessed following Western blotting, after SDS-PAGE of the void volume fraction. Anchor removal was confirmed using a commercial antibody which detects the presence of the GPI anchors (anti-CRD; Oxford Glycosystems, Zamze et al., 1988).

H. Other Methods

Proaerolysin binding was compared using an ELISA-based assay as we have described before (Rossjohn et al., 1997). Protein concentrations were measured according to Markwell et al. 1978. Total lipid phosphorous was determined following the procedure of Ames and Dubin, 1960.

2. Results

A. T-lymphocytes Lacking Thy-1 Remain Sensitive to Aerolysin

We have found that EL4 cell lines that cannot add GPI anchors to membrane proteins resist aerolysin's action and we had assumed that this was because they lacked Thy-1 (Nelson et al., 1997). We were therefore, surprised to discover that the mouse mutant T-lymphocyte cell line AKR1 (Thy-1[31] d), which does not express Thy-1 (Evans et al., 1987), was almost as sensitive to aerolysin as was the parent strain (FIG. 1). This led us to consider the possibility that aerolysin may bind to more than one GPI anchored protein in T-lymphocytes. The sensitivity of the AKR1 (Thy-1⁻ d) cell line to the toxin could then be attributed to the presence of other GPI anchored receptors, all of which would be missing from the mutant EL4 cells we studied earlier. This explanation was supported by the results of treating cells with phosphatidylinositol-specific phospholipase C, which selectively removes GPI anchored proteins from their surfaces. It may be seen in FIG. 1 that both AKR1 cell lines became less sensitive to aerolysin after treatment with the enzyme.

B. Proaerolysin Also Binds to More Than One GPI Anchored Protein in Mouse Brain

Sandwich Western blotting of mouse brain homogenate revealed that in addition to Thy-1, there is a 110 kDa membrane-associated protein that binds proaerolysin. Like Thy-1, this protein was solubilized by treating the homogenate with Pl-PLC, indicating that it too is GPI anchored. A literature search for known GPI anchored proteins of comparable size suggested that the brain protein may be neural cell adhesion molecule (NCAM; Musaka et al., 1995). More evidence for this was obtained by treating the supernatant fractions containing the 110 kDa protein released by Pl-PLC with N-glycosidase. This resulted in a decrease in the molecular weight of the proaerolysin-binding protein to approx. 90 kDa, an apparent mass consistent with the size of de-N-glycosylated NCAM which is reported to be 85 kDa (He et al., 1987. Two bands corresponding to much smaller proteins were also visible. The lower of the two bands corresponds to completely de-N-glycosylated Thy-1 and the upper may represent partially deglycosylated Thy-1 as we have discussed previously (Nelson et al., 1997), or it may represent another GPI anchored protein.

C. GPI Anchoring is a General Property of Aerolysin Receptors

Figure 2:
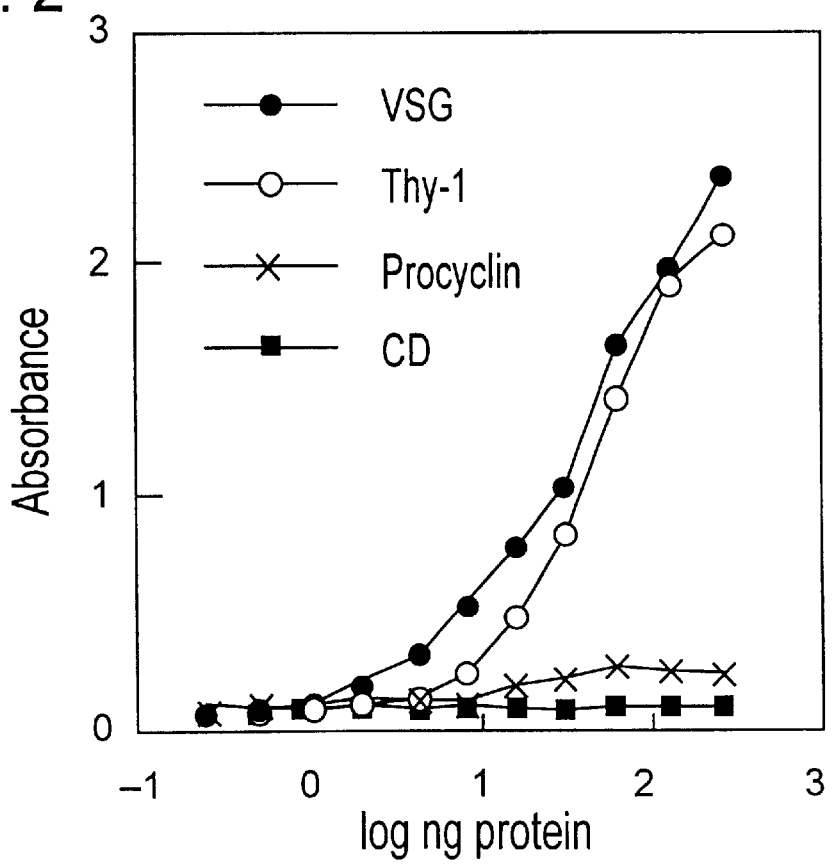
FIG. 2: shows ELISA-based assays of proaerolysin binding to GPI anchored proteins and to human cathepsin D. Each result is the mean of two experiments. In control experiments using appropriate antibodies, it was demonstrated that both procyclin and cathepsin D bound well to the plates used in these measurements.

The observation that T-cells contain at least one GPI anchored protein in addition to Thy-1 that binds proaerolysin, and that the erythrocyte aerolysin receptor (Cowell et al., 1997) and NCAM are also GPI anchored proteins, pointed to the remarkable possibility that the anchors themselves may be involved in proaerolysin binding. The variant surface glycoprotein (VSG) of *Trypanosoma brucei brucei* was the first GPI anchored protein to be characterized (Ferguson et al., 1988). Aside from its anchor, it seems to be unrelated to either Thy-1 or NCAM and it is unlikely to have any sequence homology with EAR, which appears to be a member of a small family of ADP-ribosyltransferases (Cowell et al., 1997). However, VSG has a similar, though not identical GPI anchor to Thy-1, so we felt it possible that it too could bind proaerolysin if the anchor is a binding determinant. Using samples of purified VSG and an ELISA-based assay we compared proaerolysin binding to VSG with binding to purified Thy-1. The results in FIG. 2 show that the toxin also bound the trypanosomal protein. We were easily able to detect VSG by sandwich Western blotting (not shown) in amounts comparable to the amounts of Thy-1 we have detected previously (Nelson et al., 1997).

D. Proaerolysin Cannot Bind to Thy-1 and VSG Lacking Their GPI Anchors

In order to obtain more direct evidence that the GPI anchor itself was involved in proaerolysin binding, we took two approaches. In the first, we compared protoxin binding to Thy-1 expressed in *E. coli*, which is not capable of adding GPI anchors, with binding to Thy-1 expressed in CHO cells, where we would expect processing to be normal (Ogier-Denis et al., 1995). The results showed that proaerolysin could easily detect Thy-1 expressed in the eucaryotic cell, whereas there was no evidence of specific binding to Thy-1 expressed in the bacteria, even though, as was clear from a comparison of Coomassie stained samples, far more Thy-1 was present in the *E. coli* samples we used. It is worth emphasizing that the far Western blotting procedure we used can detect less than 1 ng of native Thy-1 (Nelson et al., 1997). Of course as well as lacking the anchor, the Thy-1 expressed in the bacteria would lack the N-linked carbohydrate that is normally present in the eucaryote. However, this could not account for the difference in binding we observed, since as noted above, we have shown that the N-linked sugars apparently are not required for proaerolysin binding (Nelson et al., 1997).

In the second approach, we took advantage of the fact that HF can selectively remove nearly the entire GPI anchor from proteins without destroying the polypeptide chain (Ferguson et al., 1988). The results showed that treatment of VSG with HF led to a very large reduction in proaerolysin binding measured using sandwich Western blotting or the ELISA assay. The results also show that binding of a commercial antibody directed against the GPI determinant, which we used as a positive control of anchor removal, was also reduced.

E. Adding a GPI Anchor to a Soluble Protein Confers Proaerolysin-binding Ability A number of groups have successfully produced hybrid proteins by fusing the DNA encoding the anchor signal for a GPI anchored protein such as decay accelerating factor (DAF) or Thy-1 to the DNA encoding a protein that is normally not anchored in this way (Herick et al., 1984; Clissold 1992; Lublin and Coyn 1991). Many of these hybrid proteins appear to behave like normal GPI anchored proteins, finding their way to the exterior surface of the cell's plasma membrane. An example is cathepsin D (CD), which was converted from a soluble to a surface exposed GPI anchored protein by Ogier-Denis et al., 1995. The results in FIG. 2 show that proaerolysin has no affinity for the normal water soluble form of human CD (obtained from Sigma), nor could the soluble form of the protein be detected by sandwich Western blotting (not shown). However, the protoxin could easily detect the GPI anchored hybrid cathepsin when it was expressed in COS cells. Proaerolysin could also recognize the hybrid protein when it was released into cell-free supernatants by treating the expressing cells with PI-PLC to free it from the diglyceride portion of its foreign anchor.

F. Proaerolysin Does Not Bind to all GPI Anchored Proteins

More than 100 GPI anchored proteins are known and some cells can express several of them on their surface. For example, the human erythrocyte membrane contains at least five, DAF, complement regulatory protein (CD59), acetylcholinesterase, CAMPATH-1 (CD52), and the aerolysin receptor EAR. Interestingly, only the last of these is detected by the sandwich Western blotting procedure we used (Cowell et al., 1997; Gruber et al., 1994), suggesting that the others do not bind proaerolysin, at least under sandwich blotting conditions. Direct evidence that all GPI anchored proteins do not bind proaerolysin was obtained using purified procyclin, another trypanosomal protein with a GPI anchor that differs considerably from the anchor of VSG (Englund 1993). The results of sandwich Western blotting (not shown) and the ELISA assay (FIG. 1) showed clearly that procyclin has no affinity for proaerolysin.

G. Proaerolysin Binding Depends on the Structure of the GPI Anchor

There are two obvious reasons why proteins like procyclin and erythrocyte acetylcholinesterase may not bind proaerolysin even though they contain GPI anchors. One possibility is that the polypeptide portion of the protein also has a role to play in binding (see below). The other is that the structure of the GPI anchor itself is important in binding.

Although the structures of only a few GPI anchors are known, the available evidence indicates that there can be significant differences between species, and within species, between cells. As mentioned earlier, the anchors of brain Thy-1 and *T. brucei brucei* VSG are quite similar to each other, whereas the *T. congolense* procyclin anchor is substantially different (Englund, 1993). This is consistent with the observation that proaerolysin binds the former two proteins but not the latter. The availability of the surface protease gp63 of *L. major* in its native form with its natural anchor and expressed in CHO cells (Morrison et al., 1997), where it presumably has an anchor specific for the cell line, gave us the opportunity to determine the effect of different anchors on proaerolysin binding. Native gp63 has a GPI anchor similar to that of procyclin (Englund, 1993) and consistent with this, like the trypanosomal protein, it does not bind proaerolysin. However, gp63 expressed in the CHO cell line was easily detected with proaerolysin by sandwich Western blotting, evidence that replacing the Leishmania anchor with a mammalian one had conferred proaerolysin binding ability on the protein.

H. The Anchor Alone is not Sufficient for Proaerolysin Binding

The proteins Thy-1, NCAM, VSG, hybrid cathepsin D and gp63 have no obvious common sequence similarities, nor is it likely that any of them are related to EAR (Cowell et al., 1997). It was therefore tempting to conclude that a GPI anchor alone is sufficient for proaerolysin binding, since this is the only obvious thing that all these proteins appear to have in common. However, this would not explain why our far Western blots did not detect other erythrocyte GPI anchored proteins such as DAF and acetylcholinesterase, which presumably have the same anchor as EAR (Paturuans-Hanocq et al., 1997; Rudd et al., 1997). Nor would it explain why Thy-1 is the only obvious GPI anchored protein that binds proaerolysin in blots of AKR1 cells, in spite of the fact that the results presented in FIG. 1 show that these cells must contain at least one other GPI anchored protein that binds the protoxin. These inconsistencies suggest that some GPI anchored proteins can't be detected by proaerolysin after SDS-PAGE, at least when present in the amounts we have used, although in their native states on the cell surface, perhaps because only very small amounts are required, they may serve as receptors. This implies that the structure of the polypeptide chain may also influence proaerolysin binding. The observation of Howard and Buckley (1982) that proaerolysin binding to rat erythrocytes is reduced by treatment of the cells with proteases and the more recent observation of Cowell et al. (1997) that treatment of lipid bilayers containing the rat erythrocyter-eceptor with proteases reduces channel formation are other reasons to believe that the protein portion of the receptor is also involved in binding.

Figure 3:
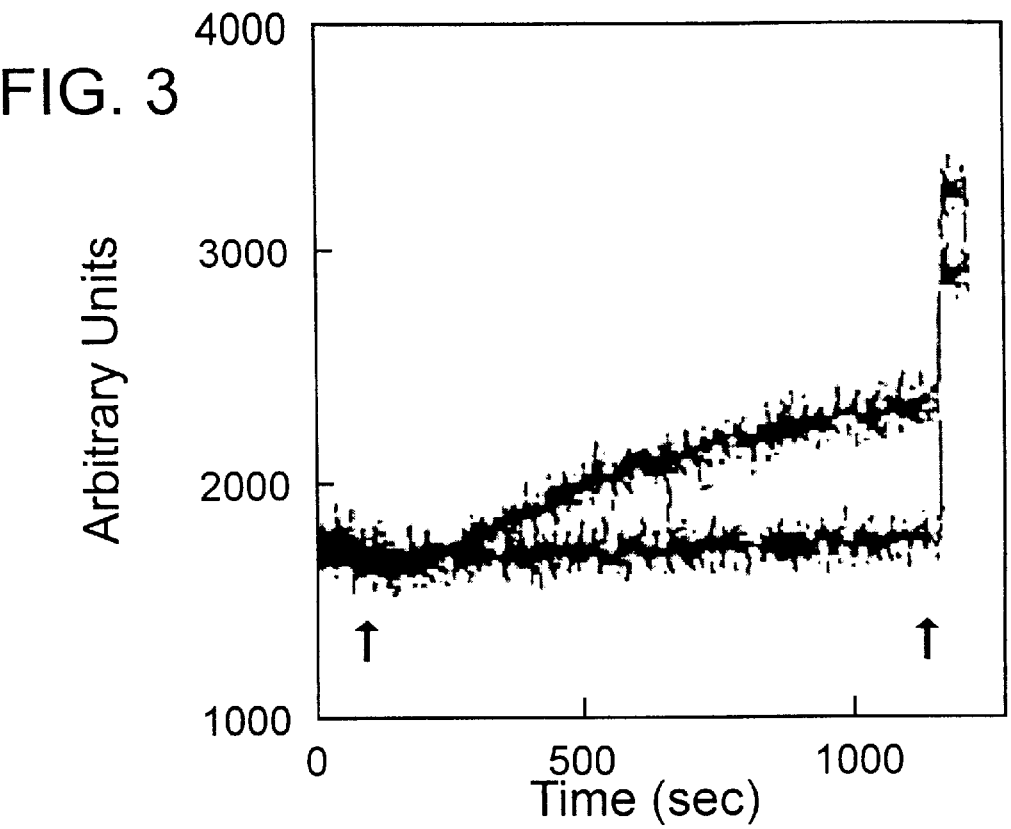
FIG. 3: shows that protease treatment of Thy-1-containing liposomes reduces their sensitivity to aerolysin. Liposomes containing reconstituted Thy-1 were treated with pronase (lower curve) and the sensitivity to aerolysin was compared with untreated liposomes (upper curve). Aerolysin (40 nM final concentration) was added at the first arrow. At the second arrow Triton X-100 was added to 0.1% (w/v) final concentration to estimate the total amount of entrapped carboxyfluorescein

Our ability to incorporate Thy-1 into liposomes (Nelson et al., 1997) gave us the opportunity to directly assess the effect of proteolysis on proaerolysin binding, by comparing aerolysin-induced dye release from liposomes containing incorporated Thy-1 with release from the same liposomes pretreated with proteases. The results are shown in FIG. 3. It may be seen that liposomes treated with protease were resistant to aerolysin at levels that caused rapid release from control liposomes.

IV. Detection of GPI Anchored Proteins, and Application to PNH Diagnosis

1. Materials and Methods

A. Cell Lines

The GPI anchor deficient lymphoblastoid cell lines, LD⁻ and JY5, harbor previously characterized PIGA mutations (Brodsky et al., 1997; Hollander et al., 1988). An expression vector containing the full-length PIGA cDNA was stably transfected into the LD⁻ and JY5 cell lines to establish the GPI anchor replete cell lines, LD⁻ (PIGA⁺) and JY5 (PIGA⁺), as previously described (Brodsky et al., 1997). All cell lines were maintained in RPMI 1640 medium (GIBCO) with 10% heat inactivated fetal calf serum. To measure CD59 expression, cells were washed in RPMI with 0.2% fetal calf serum, stained for CD59 with a fluorescein isothiocyanate-conjugated monoclonal antibody (Research Diagnostics, Flanders, N.J.) and analyzed by flow cytometry (FACscan; Becton Dickinson).

B. Preparation of Cells for Aerolysin Assay

Venous peripheral blood from patients with PNH, normal controls or disease controls was drawn into EDTA-containing tubes after informed consent as approved by the Joint Committee on Clinical Investigation of the Johns Hopkins Hospital. The blood was centrifuged at 400×g for 10 minutes and then the buffy coat was removed and the remaining erythrocytes were washed two times in phosphate buffered saline (PBS) and resuspended in PBS to a concentration of 0.8%. Peripheral blood granulocytes were isolated using Ficoll/Hypaque (density 1.11 9) as previously described by Colotta et al. (1992).

C. Titer Assay of Aerolysin-induced Hemolysis

Aerolysin ($1.5 \times 10^6$ M), produced by trypsin activation of proaerolysin as described in Garland and Buckley (1988) was diluted 1:16 in PBS to a final volume of 100 µL and added to the first well of a 96 well plate. An equal volume of PBS was then added to the first well (1:32 aerolysin) and 1:2 serial dilutions were made across the plate. 100 µL of 0.8% red cells were added to all wells and the plate was incubated at 37° C. Absorbance at 620 nm was measured using a plate reader (Biotek Instruments, Inc., Winooski, Vt.) at times 0, 5 minutes, 10 minutes, 15 minutes and 20 minutes.

D. Spectrophotometric Assay of Aerolysin-induced Hemolysis

Activated aerolysin was added to stirred cuvettes containing 1.5 mL of 0.8% v/v washed erythrocytes in phosphate buffered saline (PBS; 10 mM $NaH_2PO_4$, 150 mM NaCl, pH 7.4) to a final concentration of 8 nM. The rate of hemolysis was determined by measuring the change in optical density of the erythrocytes (which is due to a decrease in light scattering as the cells lyse) at 600 nm and 37° C. as a function of time. The instrument used was a Varian Cary 1 recording spectrophotometer.

E. Propidium Iodide Staining for Viability

Cells were suspended to $1 \times 10^6$/mL in 0.5 mL phosphate-buffered saline. 50 µL of propidium iodide (10 µg/mL in phosphate-buffered saline) were added to each tube and the mixture was incubated for 5 minutes at 37° C. Approximately 10,000 data events per sample were collected for analysis on a FACSCAN flow-cytometer (BDIS, Mansfield Mass.). Sub-cellular debris and remaining erythrocytes were excluded with a forward-scatter (FS)/900-scatter (SS) gate. Viable cells were those exhibiting no fluorescence (propidium iodide excluding).

F. Detection of Aerolysin-binding Proteins by Western Blotting

Samples of cells dissolved in sample buffer were separated by sodium dodecyl sulfate polyacrylamide electrophoresis (SDS-PAGE) using the method of Neville (1971). Proteins were blotted onto nitrocellulose and the blots were developed by sandwich Western blotting as described by Nelson et al. (1997). This involved incubation with $2 \times 10^{-8}$ M proaerolysin, followed by polyclonal anti-aerolysin and anti-rabbit horseradish peroxidase. Blots were then developed by enhanced chemiluminescence (ECL; Amersham Corp).

2. Results

A. Aerolysin-induced Hemolysis of PNH Erythrocytes

In PNH, all hematopoietic lineages have a proportion of GPI anchor deficient cells, since the PIGA mutation initially occurs in a pluripotent hematopoietic stem cell (Rosse, 1997). The proportion for individual cell types can be estimated by measuring the fraction of cells that display CD59 by flow cytometry, although this is an expensive procedure requiring complex instrumentation that is not widely available (Schubert et al., 1991; Hall and Rosse, 1996).

Figure 4C:
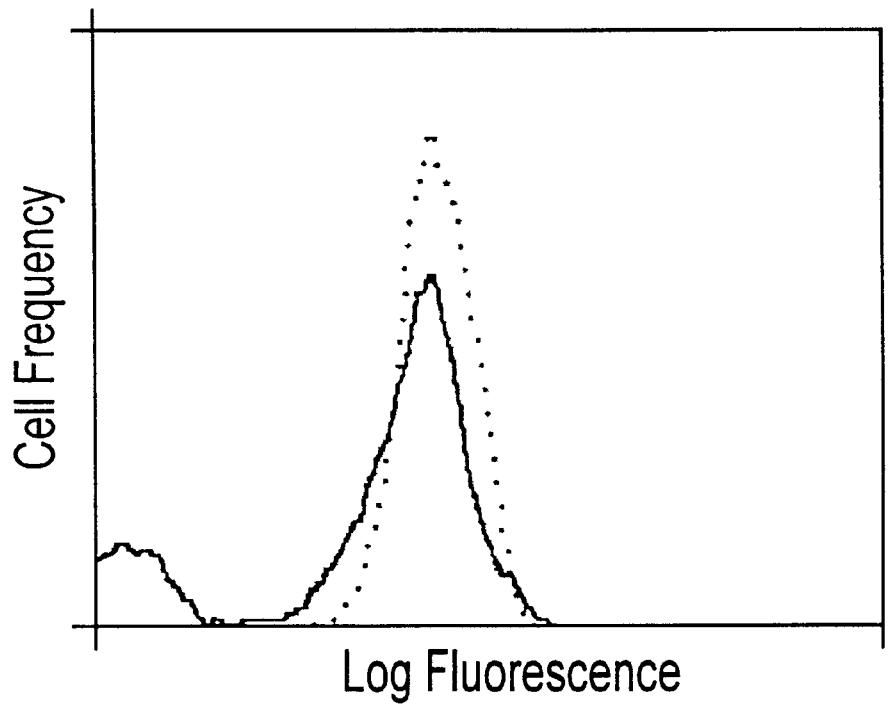
Figure 4D:
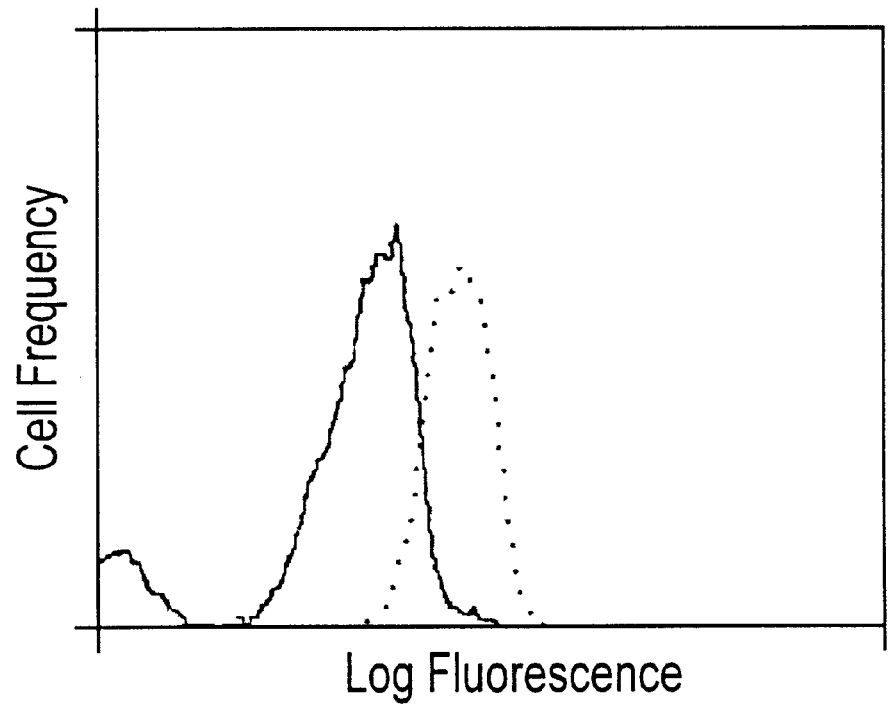

We initially performed a dose-response curve to compare the sensitivity of normal erythrocytes and PNH erythrocytes to various concentrations of aerolysin. Normal erythrocytes, but not PNH erythrocytes, were completely lysed following exposure to a 1:128 dilution of aerolysin ($1.5 \times 10^{-6}$ M stock solution) for 10 minutes at 37° C. (FIG. 4A). We also performed a kinetic analysis of normal and PNH erythrocytes following exposure to aerolysin. The spectrophotometric assay we used depends on the decrease in light scattering that accompanies erythrocyte lysis. Aerolysin (8 nM) resulted in the complete hemolysis of erythrocytes from normals within about ten minutes (FIG. 4B). The time course was highly reproducible from one normal sample to another. In contrast, all of the PNH samples we tested showed patterns that were easily distinguished from the controls (FIG. 4B). The proportion of unlysed cells, which should correspond to those cells that did not display GPI anchored proteins, could easily be calculated. For every patient, the value that was obtained corresponded very closely with the proportion of cells that lacked CD59, as determined by flow cytometry (FIG. 4B). Furthermore, flow cytometric analysis revealed that the cells remaining after exposure to aerolysin were CD59 negative (data not shown). Even in the case of the patient who had just 8% of her erythrocytes affected (estimated by measuring CD59 cells by flow cytometry) the aerolysin assay easily detected the disease.

Figure 5:
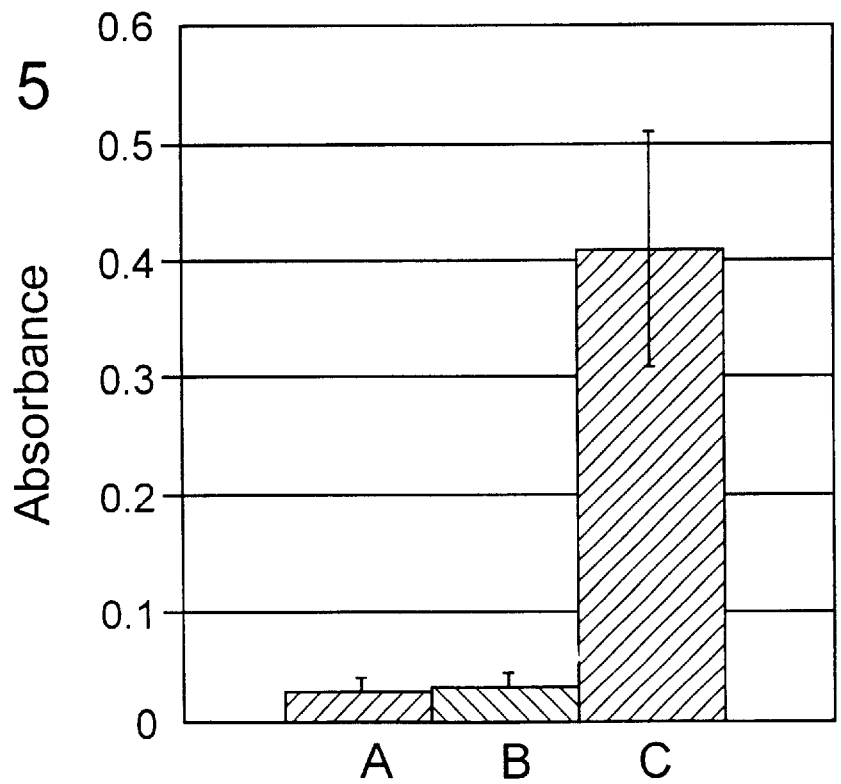
FIG. 5: shows the specificity of an aerolysin assay for PNH. A: mean absorbance of erythrocytes from 7 normal controls; B: 3 PNH patients; and C: 20 disease controls, each after exposure to a 1:128 dilution of aerolysin (1.5×10$^{-6}$ M stock solution). Disease controls consisted of myelodysplastic syndromes (7), aplastic anemia (5), polycythemia vera (2), myelofibrosis (2), sickle cell anemia (1), autoimmune hemolytic anemia (1), iron deficiency anemia (1) and acute myelogenous leukemia (1). Error bars represent standard deviation.

To determine if the assay was specific for PNH, aerolysin sensitivity of erythrocytes from patients with various hematologic disorders was measured. In every disease state we tested, including myelodysplastic syndromes, aplastic anemia, hemolytic anemias, myeloproliferative disorders and leukemias, we found that the cells were as sensitive as normal erythrocytes to the lytic effects of aerolysin (FIG. 5). An absorbance greater than 0.1 ten minutes after exposure to a 1:128 dilution of aerolysin ($1.5 \times 10^{-6}$ M stock) distinguished PNH from normals and from other hematologic disorders (FIG. 5).

B. Sensitivity of PNH Leukocytes to Aerolysin

Figure 6A:
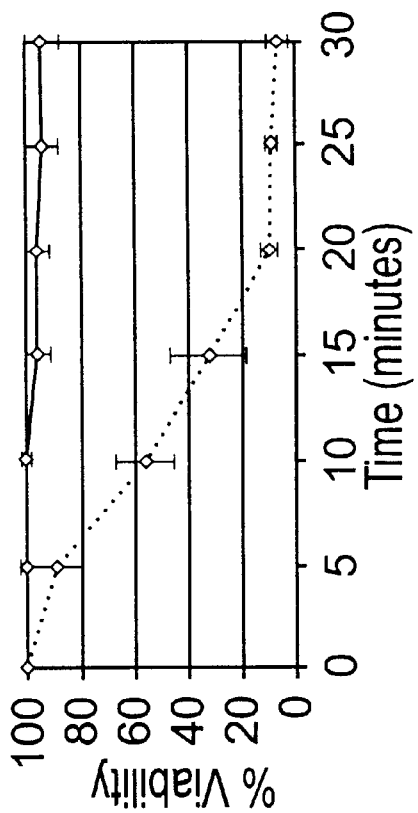
FIGS. 6A–D: show that the restoration of GPI anchor expression in PNH cell lines overcomes resistance to aerolysin.
Figure 6B:
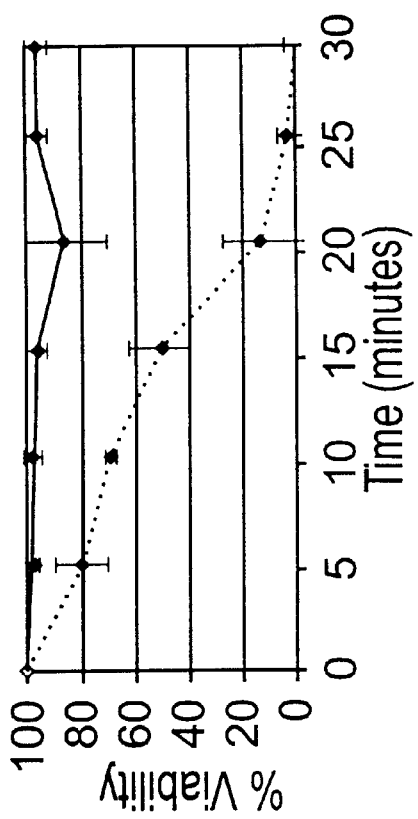
Figure 6C:
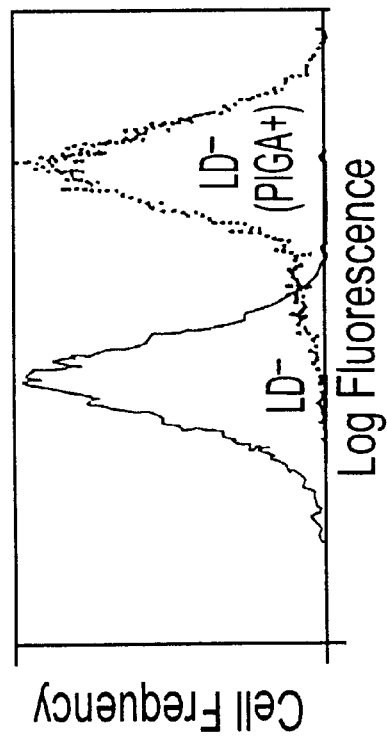
Figure 6D:
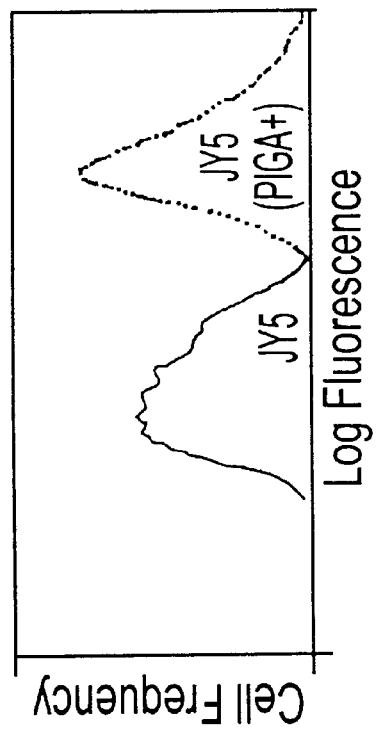

A major advantage of using flow cytometry over the PNH tests based on complement sensitivity of erythrocytes (i.e., the sucrose hemolysis and Ham's tests) is that immunophenotyping can detect abnormalities in multiple hematopoietic lineages. To determine whether the aerolysin assay could detect a GPI anchor deficiency in nucleated cells as well as in erythrocytes, the toxin was incubated with two PNH cell lines, LD⁻ and JY5, which harbor a previously characterized PIGA mutation, and hence, fail to express GPI anchored proteins. The absence of GPI anchors was confirmed using an aerolysin sandwich Western blotting procedure and flow cytometric analysis for CD59 expression (FIG. 6A and 6C). The LD⁻ and JY5 cell lines were essentially unaffected by 1 nM aerolysin (FIGS. 6B and 6D). In contrast, the same dose of aerolysin produced rapid death of the same cell lines stably transfected with the full length cDNA for PIGA (FIGS. 6B and 6D).

Figure 7B:
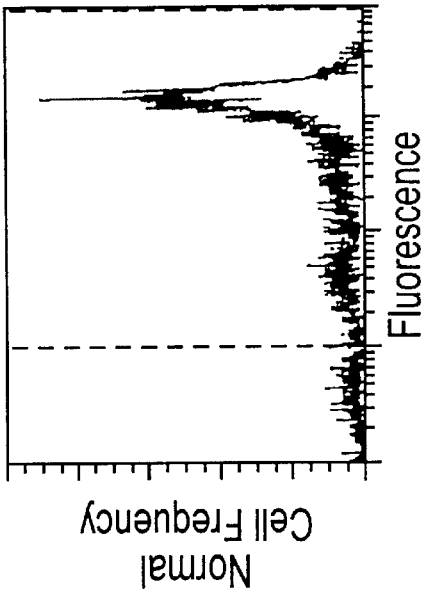
FIGS. 7A–D: show that PNH granulocytes are resistant to aerolysin. The charts show representative examples of normal and PNH granulocytes stained with propidium iodide before (A and C) and 40 minutes after (B and D) incubation with 1 nM activated aerolysin. Propidium iodide uptake was assayed using flow cytometry.
Figure 7D:
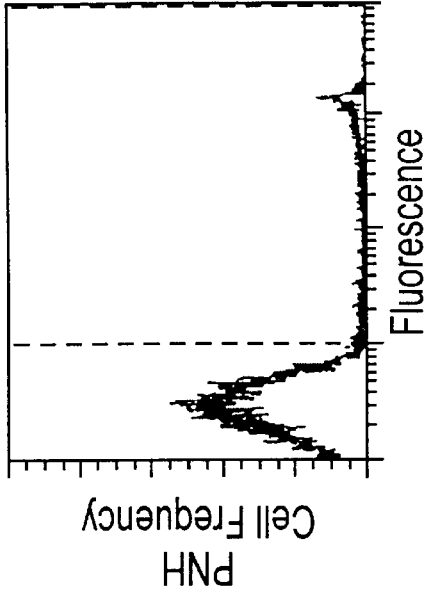
Figure 7A:
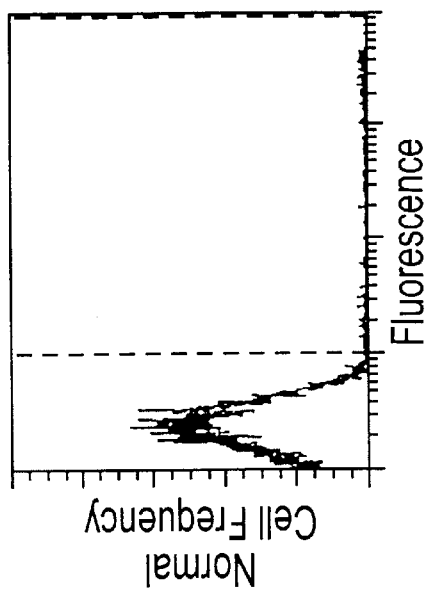
Figure 7C:
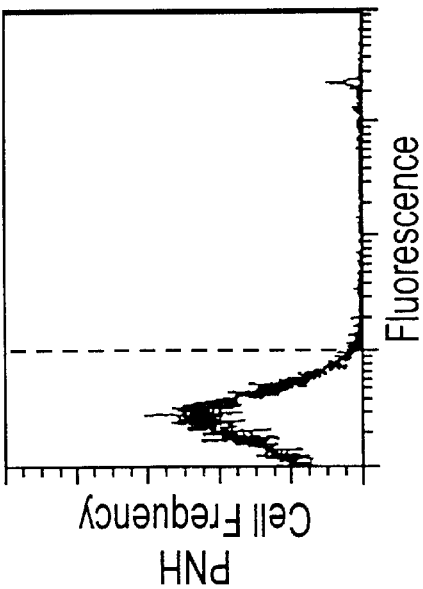

The percentage of PNH granulocytes in the circulation most accurately reflects the size of the PNH clone, since the survival of PNH granulocytes is normal or even increased (Brodxky et al., 1997; Horikawa et al., 1997; Brubaker et al., 1997) while erythrocyte survival is decreased (Rosse, 1971). Therefore, we sought to determine the sensitivity of PNH granulocytes to aerolysin. Granulocytes from patients with PNH and from normal controls were separated, treated with aerolysin and analyzed using flow cytometry to assess their ability to exclude propidium iodide. Forty minutes after exposure to 1 nM aerolysin less than 10% of normal granulocytes excluded propidium iodide (FIG. 7B). In contrast, more than 90% of PNH granulocytes retained their ability to exclude propidium iodide under identical conditions (FIG. 7D). Granulocytes from disease controls (non-PNH hematological diseases) were as sensitive to the toxin as cells from normal controls (data not shown), demonstrating that the ability to exclude propidium iodide after exposure to aerolysin was specific for PNH cells. The percentage of granulocytes that were resistant to aerolysin correlated with the percentage of cells lacking CD59 expression (data not shown).

C. Sensitivity of Aerolysin Assay for PNH

Figure 8A:
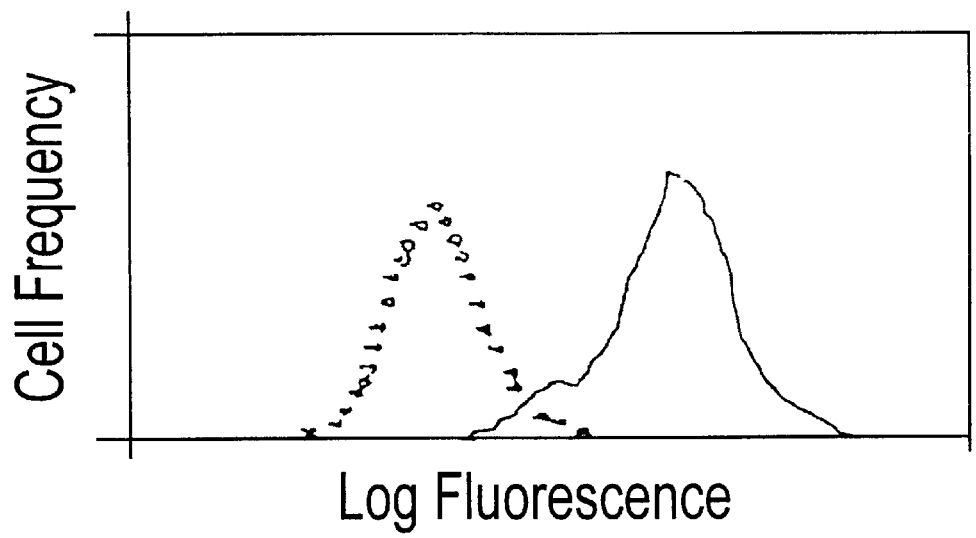
FIGS. 8A and B: illustrate the correlation between aerolysin sensitivity and flow cytometric detection of CD59 in PNH cell lines.
Figure 8B:
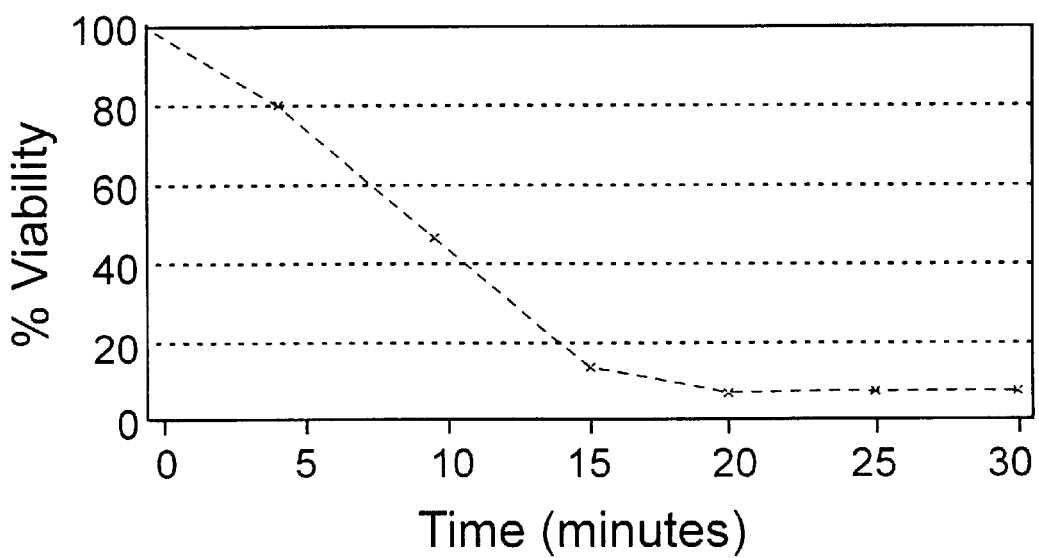
FIG. 8B shows percent viability of the LD$^-$ (solid line) and mixed cell (dotted line) populations after exposure to 1 nM aerolysin at 37° C. Cell viability was determined by trypan blue exclusion at five minute intervals.
Figure 9A:
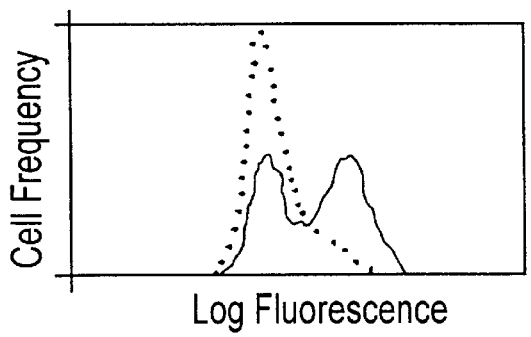
FIGS. 9A–E: show the use of aerolysin to detect small PNH populations. LD$^-$ cells (10,000) were mixed with CD59 expressing CEM cells at ratios of 1:1 (A), 1:10 (B), 1:100 (C), 1:500 (D), 1:1000 (E) and analyzed for expression of CD59 before (solid line) and after (dotted line) a 30 minute exposure to 1 nM aerolysin.
Figure 9B:
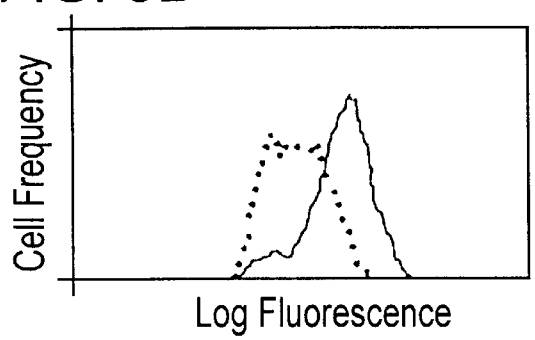
Figure 9C:
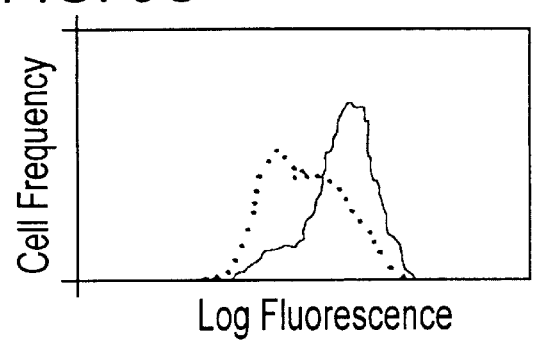
Figure 9D:
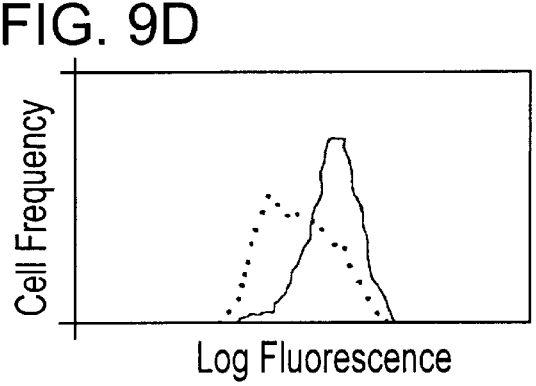
Figure 9E:
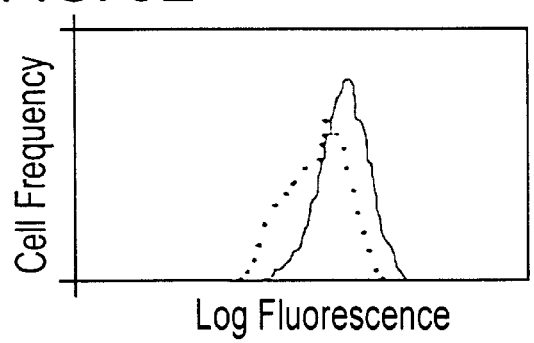

We next tested a known mixture of LD⁻ and LD⁻(PIGA⁺) to determine how accurately the new assay could determine the percentage of GPI anchor-deficient cells in a mixed population (10% PNH) cells. Similar to the above-mentioned experiments in erythrocytes, the assay accurately determined the percentage of PNH cell in the population (FIG. 8). The lower limit of detection of a PNH population using flow cytometry is 1 to 5% (Schubert et al., 1991 and Hall and Rosse, 1996). To determine whether aerolysin could detect smaller PNH populations than this, we mixed PNH cells (LD⁻) with increasing numbers of GPI anchor protein replete cells (CEM) and assayed CD59 expression before and after exposure to aerolysin (FIG. 9). Before the addition of aerolysin, PNH cells were undetectable when they comprised less than 1% of the population; however, 30 minutes after exposure to 3 nM aerolysin, PNH populations as small as 0.1% were detected.

Figure 10A:
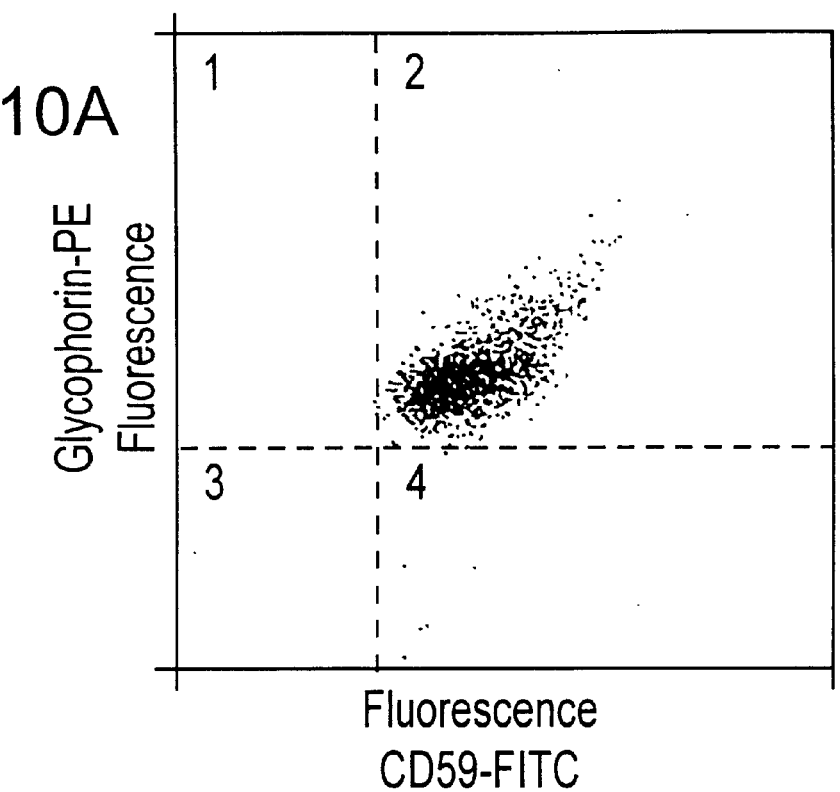
FIGS. 10A and B: show the use of aerolysin to detect a minor population of PNH cells in a patient with aplastic anemia. Two-color histogram of peripheral blood cells stained with MoAb directed against CD59 antigen (FITC) and MoAb directed against glycophorin-A (PE) before (A) and after (B) exposure to aerolysin (1.5×10$^{-9}$ mol/L for 15 minutes). Axis represent log red (PE) or log green (FITC) fluorescence intensity.
Figure 10B:
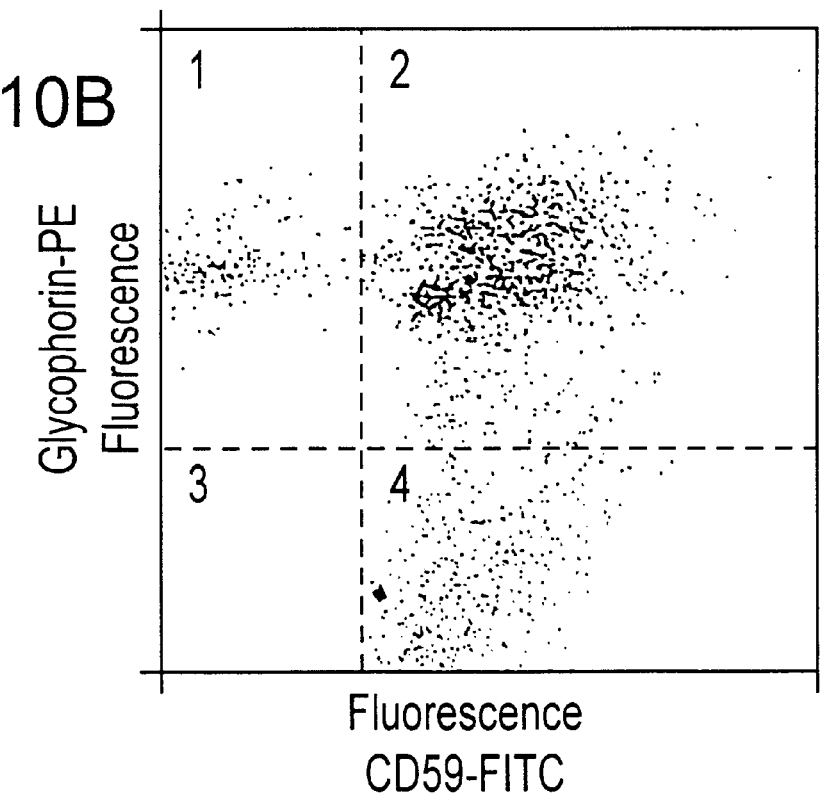
Figure 11A:
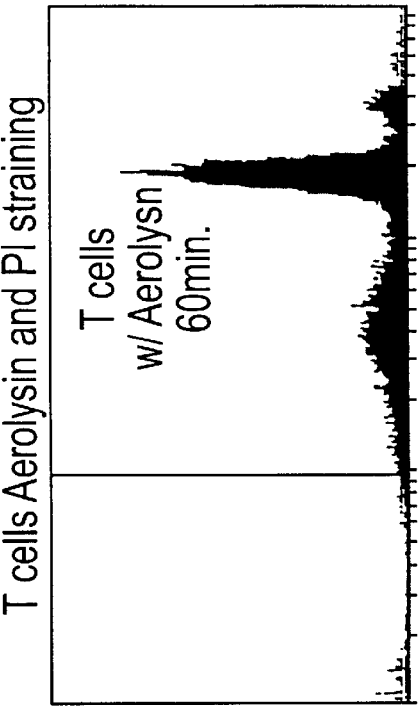
FIGS. 11A–D: show the use of a mutant non-cytolytic aerolysin molecule for the direct detection of GPI anchored proteins on cells derived from mouse thymus.
Figure 11B:
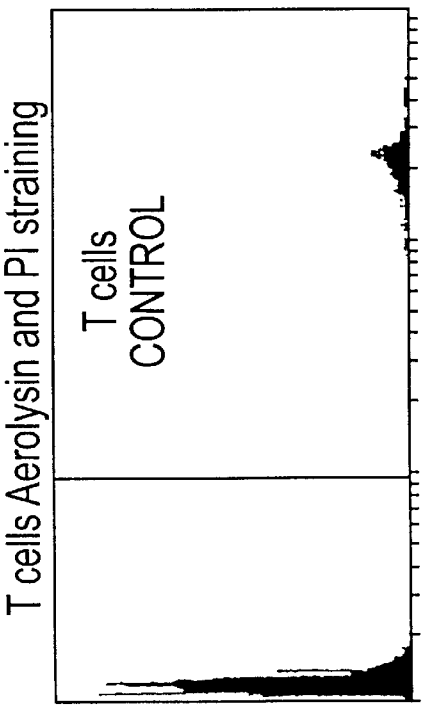
Figure 11C:
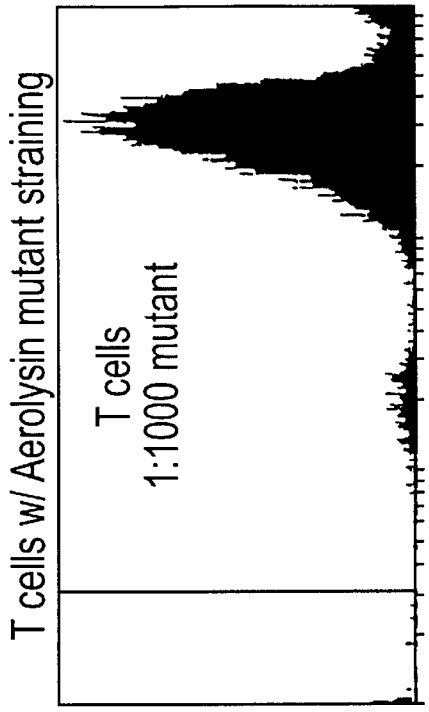
Figure 11D:
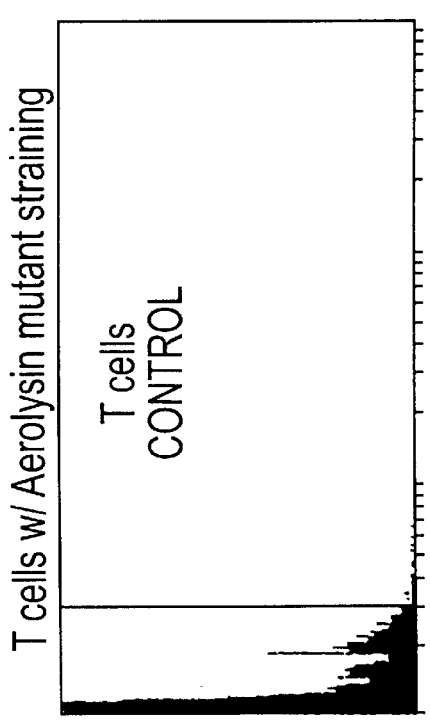
Figure 12B:
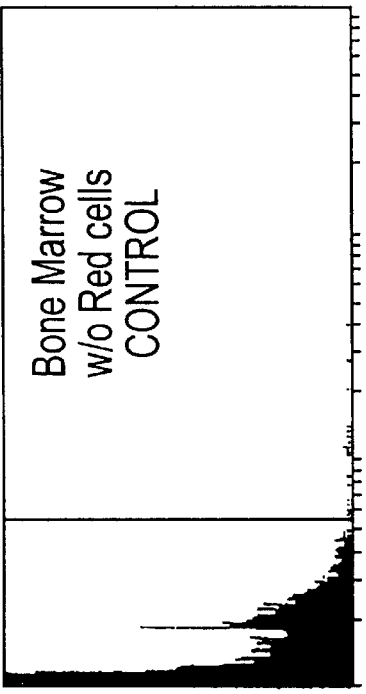
FIGS. 12A–D: show the direct detection of GPI anchored proteins on cells from bone marrow using a mutant, non-cytolytic aerolysin conjugated to Alexa 488.
Figure 12D:
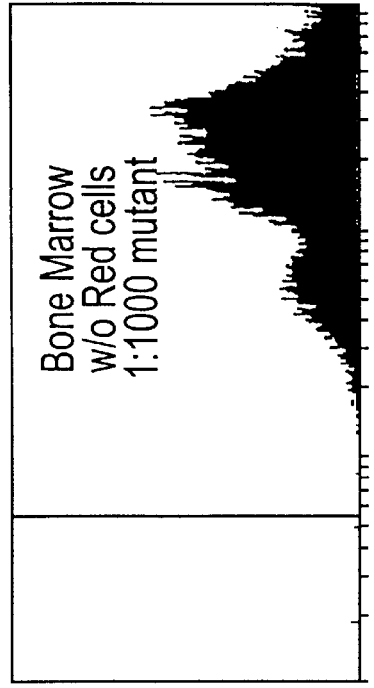
Figure 12A:
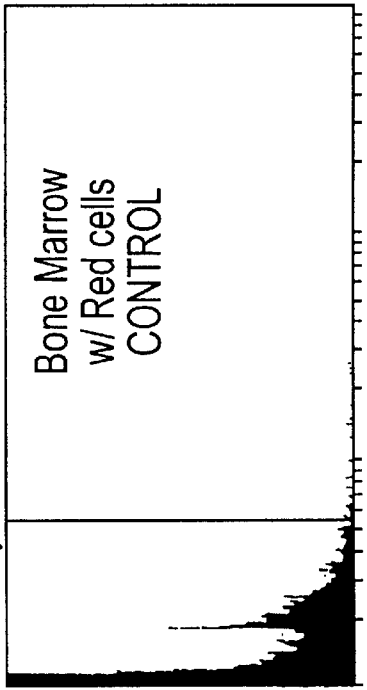
Figure 12C:
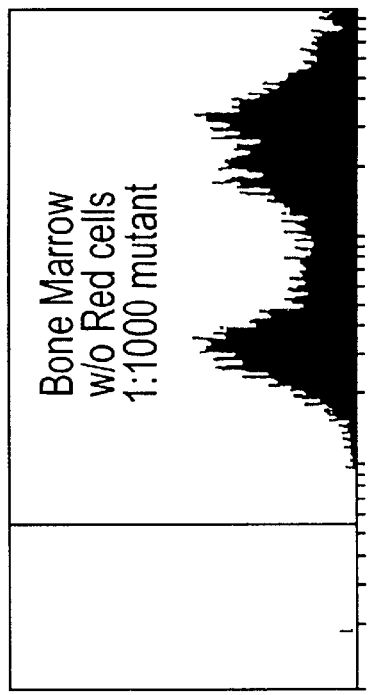

PNH can arise de novo or evolve from aplastic anemia, suggesting a pathophysiologic link between the two diseases. To test whether the use of aerolysin in conjunction with flow cytometry could detect small PNH population, we used this assay to study the peripheral blood from an aplastic anemia patient who responded poorly to immunosuppressive therapy. Before adding aerolysin, we were unable to detect PNH erythrocytes using standard flow cytometry: however, 15 minutes after exposure to $5 \times 10^{-9}$ mol/L aerolysin, a small population of PNH cells was detected (FIG. 10). Because aerolysin depleted the erthrocyte population by 2.5 to 3 logs (determined by counting on a hemacytometer), we calculated that this represents a PNH population of less that 0.075%. A similar result was obtained in a patient with a 1-year history of moderate aplastic anemia; no PNH cells could be detected in the peripheral blood of three normal control subjects treated in an identical manner (data not shown).

D. Direct Detection of GPI Anchored Proteins Using Fluorescently Labeled Aerolysin Mutant As previously stated, non-cytolytic mutant forms of toxin that bind specifically to GPI anchored proteins can be produced. These mutant toxins bind to GPI anchored proteins but do not cause cell lysis and are especially useful for direct detection of GPI anchored proteins when retention of cell viability is required. These mutant toxins may be conjugated to a detectable label to facilitate detection of toxin binding. For example, the toxin may be conjugated with a fluorescent moiety for use in FACS analyses.

In a representative experiment, the double mutant (Thy 253 Cys/Ala 300 Cys) was conjugated to Alexa 488 (Molecular Probes, Eugene, Oreg.) and the conjugated toxin was then incubated with mouse thymus cells. The results, shown in FIG. 11, indicate that conjugated toxin can be used to detect GPI anchored proteins, with a sensitivity comparable to that obtained by utilizing wild type aerolysin treatment followed by propidium iodide staining.

In another representative experiment, the conjugated mutant described above was used to detect GPI anchored proteins on cells derived from bone marrow. The results, shown in FIG. 12, indicate that the conjugated toxin was capable of detecting GPI anchored proteins on a large population of cells contained within the bone marrow extract.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

REFERENCES

1. Ames, B. N., and Dubin, D. T. J. Biol. Chem. 235, 769–775, 1960.
2. Bessler M, et al., EMBO Journal 13:110, 1994.
3. Brewis, I. A., et al., J. Biol. Chem. 270, 22946–22956, 1995.
4. Brodsky R A, et al., Blood 87:491, 1996.
5. Brodsky R A, et al., Proc Natl Acad Sci USA 94:8756, 1997.
6. Brown D A, et al., Science 245:1499, 1989.
7. Brubaker L H, et al., Blood 50:657, 1977.
8. Buckley J. T. and Howard S. P., Methods Enzymol. 165: 193–9, 1988.
9. Buckley, Bio. Chem. Cell Biol. 68:221–224, 1990.
10. Chopra et al., Can. J. Microbiol. 39, 513–523, 1993.
11. Clissold, P. M., Biochem. J. 281, 129–136, 1992.
12. Colotta F, Re F, et al., Blood 80:2012, 1992.
13. Cowell S, et al., Molecular Microbiology 25:343, 1997.
14. Cowell, S., et al., Mol. Microbiol. 25, 343–350, 1997.
15. Cullen, B. R., et al., G,. Nature 307, 241–245, 1984.
16. Dameshek W: Riddle, Blood 30:251, 1967.
17. Diep D B, et al., J Biol Chem 273:2355, 1998.
18. Englund, P. T., Ann. Rev. Biochem. 62, 121–138, 1993.
19. Engvall, Enzymol. 70:419, 1980.
20. Evans, G. A., et al., Immunogenetics 25, 28–34, 1987.
21. Ferguson, M. A. J. et al., Science 239, 753–759, 1988.
22. Ferguson, M. A. J., et al., J. Biol. Chem. 260, 14547–14555, 1985.
23. Fujita, N. et al., Cell Growth and Differentiation 6, 355–362, 1995.
24. Garland W J, Buckley J T., Infection & Immunity 56:1249, 1988.
25. Griscelli-Bennaceur A, et al., Blood 85:1354, 1995.
26. Gruber, H. J., et al., Mol. Microbiol. 14, 1093–1011, 1994.
27. Gunter, K. G., et al., J. Exp. Med. 159, 716–730, 1984.
28. Hall S E, Rosse W F., Blood 87:5332, 1996.
29. He, H-T., Finne, J., and Goridis, C., J. Cell Biol. 105, 2489–2500, 1987.
30. Hedrick, S. M., et al., Nature 308, 149–153, 1984.
31. Hirono et al., Microb. Pathog. 13, 433–446, 1992.
32. Hirono, I. and Aoki, T., Microb. Pathog. 15, 269–282, 1993.
33. Hirose, S., et al., Meth. Enzymol. 250, 582–614, 1995.
34. Hollander N, et al., J Immunol 141:4283, 1988.
35. Horikawa K, et al., Blood 90:2716, 1997.
36. Horst, M., et al., Biochem. J. 273, 355–361, 1991.
37. Howard et al., J. Bacteriol. 169, 2869–2871, 1987.
38. Howard S P, Buckley J T., Biochemistry 21:1662, 1982.
39. Howard S P, Buckley J T., Journal of Bacteriology 163:336, 1985.
40. Hueber, A., et al., J. Exp. Med. 179, 785–796, 1994.
41. Husslein et al. Mol. Microbiol. 2, 507–517, 1988.
42. Hyman, R., Trans in Genetics 4, 5–8, 1988.
43. Innis et al. (Eds.) PCR Protocals, A Guide to Methods and Applications, Academic Press, Inc., San Diego, Calif., 1990.
44. Kingston, R. E., Chapter 9 in Current Protocols in Molecular Biology. Greene publishing associates and Wiley-lnterscience, 1988.
45. Knight, P. J., et al., J. Biol. Chem. 270, 17765–17770, 1995.
46. Kohler and Milstein, Nature 256:495, 1975.
47. Kroczek, R. A., et al., J. Immunol. 136, 4379–4384, 1986.
48. Lee, J. D., et al., Proc. Natl. Acad. Sci. U.S.A 90, 9930–9934, 1993.
49. Lemansky et al., J. Cell Biol. 110, 1525–1531, 1990.
50. Letarte-Muirhead, M., et al., Biochem. J. 151, 685–697, 1975.
51. Low, M. G., et al., Biochem. J. 241, 615–619, 1987.
52. Lublin, D. M., and Coyne, K. E., J. Exp. Med. 174, 35–44, 1991.
53. Lund-Johansen, F., et al., Eur. J. Immunol. 23, 2782–2791, 1993.
54. Luzzatto L, et al., Cell 88:1, 1997.
55. Markwell, M. A., et al., Anal Biochem. 87, 206–210, 1978.
56. McConville, M. J., and Ferguson, M. A. J., Biochem. J. 294, 305–324, 1993.
57. Misumi, Y., et al., Eur. J. Biochem. 191, 563–569, 1990.
58. Miyata T, et al., Science 259:1318, 1993.
59. Miyata T, et al., N Engl J Med 330:249, 1994.
60. Morrison, C. J., et al., Biotechnol. Bioeng. 53, 594–600, 1997.
61. Mukasa, R., et al., Arch. Biochem. Biophys. 318, 182–190, 1995.
62. Nagarajan S, Brodsky R, Young NS, Medof ME., Blood 86:4656, 1995.
63. Nelson K. L., et al., J. Biol. Chem. 272, 12170–12174, 1997.
64. Neville D M., J Biol Chem 246:6328, 1971
65. Ogier-Denis, E., Bauvy, C., Couvineau, A., De Stefanis, D., Isidoro, C., and Codogno, P., Biochem. Biophys. Res. Corn. 221, 935–942, 1995.
66. Parker M W, van der Goot F G, Buckley J T., Molecular Microbiology 19:205, 1996.
67. Parker, M. W., et al., Nature 367, 292–295, 1994.
68. Parker, M. W., et al., Mol. Microbiol. 19, 205–21222, 1996.
69. Howard, S. P., and Buckley, J. T., Biochemistry 21,1662–1667, 1982.
70. Paturiaus-Hanocq, F., et al., Biochem. J. 324, 885–895, 1997.
71. Powell SK, et al., Nature 353:76, 1991.
72. Pu, M., et al., FEBS Lett. 361, 295–298, 1995.
73. Roberts, W. L., et al., Proc. Natl. Acad. Sci. U.S.A. 84, 7817–7821, 1987.
74. Robinson P J., Immunology Today 12:35, 1991.
75. Rosse W F, Ware R E., Blood 86:3277, 1995.

76. Rosse W F., Blood 37:556, 1971.
77. Rosse W F., Blood 60:20, 1982.
78. Rosse W F., Medicine 76:63, 1997.
79. Rossjohn, J., et al., EMBO J. 16, 3426–3434, 1997.
80. Rotoli B, Luzzatto L., Bailliere's Clinical Haematology 2:113, 1989.
81. Rudd, P. M., et al., J. Biol. Chem. 272, 7229–7244, 1997.
82. Schubert J, et al., Br J Haematol 79:487, 1991.
83. Seki et al., Proc. Natl. Acad. Sci. U.S.A. 82, 6657–6661, 1985.
84. Socie G, et al., N Engl J Med 329:1152, 1993.
85. Socie G, et al., French Society of Haematology [see comments]. Lancet 348:573,1996.
86. Solomon, K. R., et al., Proc. Natl. Acad. Sci. U.S.A. 93, 6053–6058, 1996.
87. Stefanova I, et al., Science 254:1016, 1991.
88. Stefanova, I., et al., J. Biol. Chem. 268, 20725–20728, 1993.
89. Stefanova, I., et al., Science 254, 1016–1018, 1991.
90. Sugiyama et al., J. Biol. Chem. 266, 12119–12122, 1991.
91. Takeda J, et al., Cell 73:703, 1993.
92. Tobias, P. S., and Ulevitch, R. J., Immunobiology 187, 227–232, 1993.
93. Ulevitch, R. J., and Tobias, P. S., Annu. Rev. Immunol. 13, 437–457, 1995.
94. van der Goot F G, et al., Biochemistry 32:2636, 1993.
95. Wang, X., et al., Biochemistry 35, 16305–16312, 1996.
96. Young N S, Blood 79:1385, 1992.
97. Zamze, S. E., et al., Eur. J. Biochem. 176, 527–534, 1988.
98. Zang, F., et al., Proc. Natl. Acad. Sci. U.S.A. 89, 5231–5235, 1992.

What is claimed is:

1. A method for detecting the presence or absence of a Paroxysmal Nocturnal Hemoglobinurea (PNH)-affected cell in a biological sample containing blood cells, comprising:
   contacting the biological sample with aerolysin;
   detecting binding of the aerolysin to the blood cells; and
   quantifying the binding of aerolysin to the blood cells, wherein decreased binding of the aerolysin to the blood cells compared to binding observed with a control blood sample indicates the presence of PNH-affected cells.

2. The method of claim 1 wherein the aerolysin is conjugated to a detectable label.

3. The method of claim 2 wherein the binding of the aerolysin to the blood cells is detected by flow cytometry.

4. The method of claim 1 wherein detecting the binding is achieved by detecting lysis of the blood cells, wherein a decrease in optical density compared to a control blood sample indicates the absence of PNH-affected cells in the biological sample.

5. The method of claim 4 wherein the lysis is detected by visual inspection.

6. The method of claim 4 wherein the lysis is detected by use of a microtiter plate reader.

7. The method of claim 1, wherein detecting the binding is achieved by detecting lysis of the blood cells, wherein a reduced rate or amount of lysis of the blood cells compared to lysis observed with a control blood sample indicates a presence of PNH-affected cells in the biological sample.

8. The method of claim 1 wherein the biological sample is whole blood.

9. The method of claim 1 wherein the biological sample is erythrocytes or granulocytes.

10. The method of claim 2, wherein the detectable label is a fluorescent label.

11. The method of claim 1, wherein contacting the biological sample with aerolysin increases the relative concentration of PNH-affected cells due to lysis of the non-PNH-affected cells.

12. The method of claim 1, wherein the aerolysin is a non-cytolytic form of aerolysin.

13. The method of claim 12, wherein the non-cytolytic form of aerolysin is conjugated to a fluorescent label.

14. The method of claim 12, further comprising separating cells to which the non-cytolytic form of aerolysin is bound from cells to which the a non-cytolytic form of aerolysin is not bound.

15. The method of claim 14, wherein the separation is achieved by fluorescence activated cell sorting (FACS).

* * * * *

UNITED STATES PATENT AND TRADEMARK OFFICE
CERTIFICATE OF CORRECTION

PATENT NO.     : 6,593,095 B1
DATED          : July 15, 2003
INVENTOR(S)    : Buckley et al.

It is certified that error appears in the above-identified patent and that said Letters Patent is hereby corrected as shown below:

Column 12,
Line 54, "Thy-1$^{31}$ d)" should be -- (Thy-1$^-$ d) --

Column 13,
Line 17, "1987." should read -- 1987). --

Column 15,
Lines, 45-46, "erythrocytereceptor" should be -- erythrocyte receptor --

Column 16,
Line 19, "(density 1.11 9)" should be -- (density 1.119) --
Line 22, "(1.5x106M)" should be -- (1.5x10$^{-6}$ M) --

Column 17,
Line 36, "CD59" should read -- CD59$^-$ --

Column 20,
Line 52, "Corn." should be -- Com. --

Signed and Sealed this

Twenty-first Day of September, 2004

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 2346
<212> TYPE: DNA
<213> ORGANISM: Aeromonas sp.
<220> FEATURE:
<221> NAME/KEY: CDS
<222> LOCATION: (532)..(1989)

<400> SEQUENCE: 1
cgccccgagt cagctgcggc cgttcactcg cgacgggcac aggcccttg      60
cttgcggtgg ccggtcactc gctgcaattg caggggttgg gcacaatcac cttcgatgcc      120
ggcacccgct ggctcaacgg cggtcccgcc gatctgcaac cgggtcgcca actggtgctg      180
agccgcgatg aaacgggtcg ggcaaccgag atcctgatcc ccaacccga ggatgaaccg       240
gaataaggat catgcagcca aacgcttaat atttattttg ctaaattaga aatttctttt      300
ttatctatat tccaaaagat gattaagtga cgaataaaat aatagagcga gtgctctgat      360
attatatcaa tcaatattga atgaagttca atttatgatt ttgttaatat attgcgcata      420
ttaaaatgtg ggctggatcg catattgaga ttaatctcac tgatattgtc gtactcacat      480
gccacccgct gatatataag gttggtgaat gcatgtcaat gttcaatata ttggggttgc     537
t atg caa
  Met Gln
  1 aaa ata aaa cta act ggc ttg tca tta atc ata tcc ggc ctg ctg atg   585
Lys Ile Lys Leu Thr Gly Leu Ser Leu Ile Ile Ser Gly Leu Leu Met
      5                   10                  15 gca cag gcg caa gcg gca gag ccc gtc tat cca gac cag ctt cgc ttg   633
Ala Gln Ala Gln Ala Ala Glu Pro Val Tyr Pro Asp Gln Leu Arg Leu
 20                  25                  30 ttt tca ttg ggc caa ggg gtc tgt ggc gac aag tat cgc ccc gtc aat   681
Phe Ser Leu Gly Gln Gly Val Cys Gly Asp Lys Tyr Arg Pro Val Asn
 35                  40                  45                  50 cga gaa gaa gcc caa agc gtt aaa agc aat att gtc ggc atg atg ggg   729
Arg Glu Glu Ala Gln Ser Val Lys Ser Asn Ile Val Gly Met Met Gly
             55                  60                  65 caa tgg caa ata agc ggg ctg gcc aac ggc tgg gtc att atg ggg ccg   777
Gln Trp Gln Ile Ser Gly Leu Ala Asn Gly Trp Val Ile Met Gly Pro
         70                  75                  80 ggt tat aac ggt gaa ata aaa cca ggg aca gcg tcc aat acc tgg tgt   825
Gly Tyr Asn Gly Glu Ile Lys Pro Gly Thr Ala Ser Asn Thr Trp Cys
     85                  90                  95
```

```
tat ccg acc aat cct gtt acc ggt gaa ata ccg aca ctg tct gcc ctg    873
Tyr Pro Thr Asn Pro Val Thr Gly Glu Ile Pro Thr Leu Ser Ala Leu
        100                 105                 110 gat att cca gat ggt gac gaa gtc gat gtg cag tgg cga ctg gta cat    921
Asp Ile Pro Asp Gly Asp Glu Val Asp Val Gln Trp Arg Leu Val His
115                 120                 125                 130 gac agt gcg aat ttc atc aaa cca acc agc tat ctg gcc cat tac ctc    969
Asp Ser Ala Asn Phe Ile Lys Pro Thr Ser Tyr Leu Ala His Tyr Leu
                135                 140                 145 ggt tat gcc tgg gtg ggc ggc aat cac agc caa tat gtc ggc gaa gac   1017
Gly Tyr Ala Trp Val Gly Gly Asn His Ser Gln Tyr Val Gly Glu Asp
            150                 155                 160 atg gat gtg acc cgt gat ggc gac ggc tgg gtg atc cgt ggc aac aat   1065
Met Asp Val Thr Arg Asp Gly Asp Gly Trp Val Ile Arg Gly Asn Asn
                165                 170                 175 gac ggc ggc tgt gac ggc tat cgc tgt ggt gac aag acg gcc atc aag   1113
Asp Gly Gly Cys Asp Gly Tyr Arg Cys Gly Asp Lys Thr Ala Ile Lys
180                 185                 190 gtc agc aac ttc gcc tat aac ctg gat ccc gac agc ttc aag cat ggc   1161
Val Ser Asn Phe Ala Tyr Asn Leu Asp Pro Asp Ser Phe Lys His Gly
195                 200                 205                 210 gat gtc acc cag tcc gac cgc cag ctg gtc aag act gtg gtg ggc tgg   1209
Asp Val Thr Gln Ser Asp Arg Gln Leu Val Lys Thr Val Val Gly Trp
                215                 220                 225 gcg gtc aac gac agc gac acc ccc caa tcc ggc tat gac gtc acc ctg   1257
Ala Val Asn Asp Ser Asp Thr Pro Gln Ser Gly Tyr Asp Val Thr Leu
            230                 235                 240 cgc tac gac aca gcc acc aac tgg tcc aag acc aac acc tat ggc ctg   1305
Arg Tyr Asp Thr Ala Thr Asn Trp Ser Lys Thr Asn Thr Tyr Gly Leu
                245                 250                 255 agc gag aag gtg acc acc aag aac aag ttc aag tgg cca ctg gtg ggg   1353
Ser Glu Lys Val Thr Thr Lys Asn Lys Phe Lys Trp Pro Leu Val Gly
260                 265                 270 gaa acc caa ctc tcc atc gag att gct gcc aat cag tcc tgg gcg tcc   1401
Glu Thr Gln Leu Ser Ile Glu Ile Ala Ala Asn Gln Ser Trp Ala Ser
275                 280                 285                 290 cag aac ggg ggc tcg acc acc acc tcc ctg tct cag tcc gtg cga ccg   1449
Gln Asn Gly Gly Ser Thr Thr Thr Ser Leu Ser Gln Ser Val Arg Pro
            295                 300                 305 act gtg ccg gcc cgc tcc aag atc ccg gtg aag ata gag ctc tac aag   1497
Thr Val Pro Ala Arg Ser Lys Ile Pro Val Lys Ile Glu Leu Tyr Lys
                310                 315                 320 gcc gac atc tcc tat ccc tat gag ttc aag gcc gat gtc agc tat gac   1545
Ala Asp Ile Ser Tyr Pro Tyr Glu Phe Lys Ala Asp Val Ser Tyr Asp
                325                 330                 335 ctg acc ctg agc ggc ttc ctg cgc tgg ggc ggc aac gcc tgg tat acc   1593
Leu Thr Leu Ser Gly Phe Leu Arg Trp Gly Gly Asn Ala Trp Tyr Thr
340                 345                 350 cac ccg gac aac cgt ccg aac tgg aac cac acc ttc gtc ata ggt ccg   1641
His Pro Asp Asn Arg Pro Asn Trp Asn His Thr Phe Val Ile Gly Pro
355                 360                 365                 370 tac aag gac aag gcg agc agc att cgg tac cag tgg gac aag cgt tac   1689
Tyr Lys Asp Lys Ala Ser Ser Ile Arg Tyr Gln Trp Asp Lys Arg Tyr
            375                 380                 385 atc ccg ggt gaa gtg aag tgg tgg gac tgg aac tgg acc ata cag cag   1737
Ile Pro Gly Glu Val Lys Trp Trp Asp Trp Asn Trp Thr Ile Gln Gln
                390                 395                 400 aac ggt ctg tct acc atg cag aac aac ctg gcc aga gtg ctg cgc ccg   1785
Asn Gly Leu Ser Thr Met Gln Asn Asn Leu Ala Arg Val Leu Arg Pro
```

```
                    405                 410                 415
gtg cgg gcg ggg atc acc ggt gat ttc agt gcc gag agc cag ttt gcc    1833
Val Arg Ala Gly Ile Thr Gly Asp Phe Ser Ala Glu Ser Gln Phe Ala
    420                 425                 430 ggc aac ata gag atc ggt gct ccc gtg ccg ctc gcg gct gac agc aag    1881
Gly Asn Ile Glu Ile Gly Ala Pro Val Pro Leu Ala Ala Asp Ser Lys
435                 440                 445                 450 gtg cgt cgt gct cgc agt gtg gac ggc gct ggt caa ggc ctg agg ctg    1929
Val Arg Arg Ala Arg Ser Val Asp Gly Ala Gly Gln Gly Leu Arg Leu
                455                 460                 465 gag atc ccg ctc gat cgc gaa gag ctc tcc ggg ctt ggc ttc aac aag    1977
Glu Ile Pro Leu Asp Arg Glu Glu Leu Ser Gly Leu Gly Phe Asn Lys
            470                 475                 480 tca gcc tca gcg tgaccctgc tgccaatcaa taacggcagc gcgttgtagt        2029
Ser Ala Ser Ala
        485 gatggaaccg ggcctctgtg gcccggtttt tgtttgcact ggtcgggctt gttaaaggct    2089 tgtgctttcc atttccccac ttatactggc gccatcttgt cggagtgcca accgtcgaac    2149 gacgcgaggc tgagaccgtt aattcgggat ccgtgcaacc tcatcaggct agcacctgcg    2209 aagggaaaca aggtaactt gcgggttgcc gcgccggggg agggacaagc ctctccgcgt     2269 catcaagagg agccattcct cgatgagtca gggcgcacaa gagggactct gtcccgtccg    2329 gtctgcccag gaggggc                                                   2346

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 2
atgcaaaaaa taaaactaac tggcttg                                         27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 3
cgctgaggct gacttgaacg gaagccc                                         27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 4
gggaattcca tatgcagaag gtgaccagcc                                      30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 5
```

```
ccggaattca acacttgacc agtttgtctc                                          30

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 6
aagcttgctg cagcagcgga agac                                                24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 7
ctagaggatc ccaccagtca cagggac                                             27
```